(12) United States Patent
Kuhn et al.

(10) Patent No.: US 10,613,089 B2
(45) Date of Patent: Apr. 7, 2020

(54) METHOD OF USING NON-RARE CELLS TO DETECT RARE CELLS

(71) Applicants: The Scripps Research Institute, La Jolla, CA (US); Epic Sciences, Inc., San Diego, CA (US)

(72) Inventors: Peter Kuhn, Solana Beach, CA (US); Anand Kolatkar, San Diego, CA (US); Joshua Kunken, San Diego, CA (US); Dena Marrinucci, San Diego, CA (US); Xing Yang, San Diego, CA (US); John R. Stuelpnagel, Santa Barbara, CA (US)

(73) Assignees: The Scripps Research Institute, La Jolla, CA (US); Epic Sciences, Inc., San Diego, CA (US)

( * ) Notice: Subject to any disclaimer, the term of this patent is extended or adjusted under 35 U.S.C. 154(b) by 0 days.

(21) Appl. No.: 16/252,472

(22) Filed: Jan. 18, 2019

(65) Prior Publication Data
US 2019/0257834 A1 Aug. 22, 2019

Related U.S. Application Data

(63) Continuation of application No. 15/601,696, filed on May 22, 2017, which is a continuation of application No. 13/503,014, filed as application No. PCT/US2010/053431 on Oct. 20, 2010, now abandoned, application No. 16/252,472, which is a continuation-in-part of application No. 15/710,102, filed on Sep. 20, 2017, which is a continuation of application No. 12/223,351, filed as application No. PCT/US2007/002798 on Jan. 30, 2007, now abandoned.

(60) Provisional application No. 61/253,787, filed on Oct. 21, 2009, provisional application No. 60/763,625, filed on Jan. 30, 2006.

(51) Int. Cl.
*G01N 33/573* (2006.01)
*G01N 33/574* (2006.01)
*G01N 33/50* (2006.01)
*G01N 33/68* (2006.01)

(52) U.S. Cl.
CPC ....... *G01N 33/574* (2013.01); *G01N 33/5076* (2013.01); *G01N 33/5091* (2013.01); *G01N 33/6875* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | |
|---|---|---|
| 6,197,523 B1 | 3/2001 | Rimm et al. |
| 6,701,197 B2 | 3/2004 | Ben-Ezra et al. |
| 6,960,449 B2 | 11/2005 | Wang et al. |
| 7,277,569 B2 | 10/2007 | Bruce et al. |
| 7,280,261 B2 | 10/2007 | Curry et al. |
| 7,282,180 B2 | 10/2007 | Tibbe et al. |
| 7,305,112 B2 | 12/2007 | Curry et al. |
| 7,546,210 B2 | 6/2009 | Callahan et al. |
| 7,724,937 B2 | 5/2010 | So et al. |
| 7,943,397 B2 | 5/2011 | Tibbe et al. |
| 8,088,715 B2 | 1/2012 | Bodmer et al. |
| 2001/0018058 A1 | 8/2001 | Reed et al. |
| 2002/0098535 A1 | 7/2002 | Wang et al. |
| 2002/0160443 A1 | 10/2002 | Tsipouras et al. |
| 2002/0187485 A1 | 12/2002 | Jakobsen et al. |
| 2003/0108529 A1 | 6/2003 | Nackman et al. |
| 2003/0109059 A1 | 6/2003 | Adrien et al. |
| 2003/0109420 A1 | 6/2003 | Valkirs et al. |
| 2003/0129676 A1 | 7/2003 | Terstappen et al. |
| 2004/0029213 A1 | 2/2004 | Callahan |
| 2005/0003464 A1 | 1/2005 | Tibbe et al. |
| 2005/0181463 A1 | 8/2005 | Rao et al. |
| 2006/0024756 A1 | 2/2006 | Tibbe et al. |
| 2007/0212698 A1 | 9/2007 | Bendele et al. |
| 2007/0212736 A1 | 9/2007 | Chen-Kiang et al. |
| 2008/0009019 A1 | 1/2008 | Haizlip et al. |
| 2008/0076727 A1 | 3/2008 | Hoon et al. |
| 2008/0090239 A1 | 4/2008 | Shoemaker et al. |
| 2008/0113358 A1 | 5/2008 | Kapur et al. |
| 2009/0029378 A1 | 1/2009 | Connelly et al. |
| 2009/0072171 A1 | 3/2009 | So et al. |
| 2009/0081688 A1 | 3/2009 | Luo et al. |

(Continued)

FOREIGN PATENT DOCUMENTS

| | | |
|---|---|---|
| CN | 1596265 A | 3/2005 |
| CN | 101099104 A | 1/2008 |

(Continued)

OTHER PUBLICATIONS

Meng et al (Clin Can Res 10:8152-8162, 2004 (Year: 2004).*
Racila et al (PNAS 95:4589-4594, 1998). (Year: 1998).*
Shaffer et al (Clin Cancer Res 13:2023-29, 2007 (Year: 2007).*
Leversha et al (Clin Cancer Res. 15; 15(6): 2091-2097, Mar. 2009). (Year: 2009).*
Aberle et al., "Reduced lung-cancer mortality with low-dose computed tomographic screening," *N. Engl. J. Med.*, 365(5):395-409 (2011).
Aggarwal et al., "Neuroendocrine prostate cancer: subtypes, biology, and clinical outcomes," *J. Natl. Compr. Canc. Netw.*, 12(5):719-726 (2014).

(Continued)

*Primary Examiner* — Lei Yao
(74) *Attorney, Agent, or Firm* — Jones Day

(57) ABSTRACT

The invention provides seminal computational approaches utilizing data from non-rare cells to detect rare cells, such as circulating tumor cells (CTCs). The invention is applicable at two distinct stages of CTC detection; the first being to make decisions about data collection parameters and the second being to make decisions during data reduction and analysis. Additionally, the invention utilizes both one and multi-dimensional parameterized data in a decision making process.

9 Claims, 5 Drawing Sheets

(56) References Cited

U.S. PATENT DOCUMENTS

| | | |
|---|---|---|
| 2009/0105963 A1 | 4/2009 | Laursen et al. |
| 2009/0317836 A1 | 12/2009 | Kuhn et al. |
| 2010/0028915 A1 | 2/2010 | Gualberto et al. |
| 2010/0048709 A1 | 2/2010 | Wafa et al. |
| 2010/0184093 A1 | 7/2010 | Donovan et al. |
| 2010/0184629 A1 | 7/2010 | Giffin et al. |
| 2010/0297634 A1 | 11/2010 | Chen |
| 2010/0300216 A1 | 12/2010 | Angros |
| 2011/0189670 A1 | 8/2011 | Katz et al. |
| 2011/0238325 A1 | 9/2011 | Lett et al. |
| 2011/0300551 A1 | 12/2011 | Rao et al. |
| 2012/0208706 A1 | 8/2012 | Lipson et al. |
| 2012/0276555 A1 | 11/2012 | Kuhn et al. |
| 2013/0078667 A1 | 3/2013 | Goodman et al. |
| 2013/0130241 A1 | 5/2013 | Dehm |
| 2013/0157347 A1 | 6/2013 | Topol et al. |
| 2013/0171642 A1 | 7/2013 | Pestano et al. |
| 2013/0252259 A1 | 9/2013 | Kuhn et al. |
| 2014/0024024 A1 | 1/2014 | Sood et al. |
| 2014/0031250 A1 | 1/2014 | Ting et al. |
| 2014/0308669 A1 | 10/2014 | Yang et al. |
| 2014/0329917 A1 | 11/2014 | Marienfeld et al. |
| 2015/0147339 A1 | 5/2015 | Olson et al. |
| 2015/0185204 A1 | 7/2015 | Kuhn et al. |
| 2015/0212089 A1 | 7/2015 | Dittamore |
| 2015/0233927 A1 | 8/2015 | Giannakakou et al. |
| 2016/0033508 A1 | 2/2016 | Dittamore |
| 2016/0040245 A1 | 2/2016 | Dittamore |
| 2016/0266127 A1 | 9/2016 | Kuhn et al. |
| 2016/0341732 A1 | 11/2016 | Dittamore |
| 2017/0010268 A1 | 1/2017 | Marrinucci |
| 2017/0192003 A1 | 7/2017 | Kuhn et al. |
| 2017/0242016 A1 | 8/2017 | Dittamore |
| 2017/0285035 A1 | 10/2017 | Dittamore |
| 2018/0052167 A1 | 2/2018 | Dittamore |
| 2018/0100857 A1 | 4/2018 | Kuhn et al. |
| 2018/0155794 A1 | 6/2018 | Dittamore et al. |
| 2018/0321247 A1 | 11/2018 | Dittamore et al. |
| 2019/0025312 A1 | 1/2019 | Dittamore et al. |

FOREIGN PATENT DOCUMENTS

| | | |
|---|---|---|
| CN | 101511481 A | 8/2009 |
| CN | 101226118 B | 6/2010 |
| EP | 0919812 A2 | 6/1999 |
| WO | WO 1999/41613 A1 | 8/1999 |
| WO | WO 2006/041453 A1 | 4/2006 |
| WO | WO 2007/008446 A2 | 1/2007 |
| WO | WO 2007/089911 A2 | 8/2007 |
| WO | WO 2008/030381 A2 | 3/2008 |
| WO | WO 2008/133666 A2 | 11/2008 |
| WO | WO 2009/051734 | 4/2009 |
| WO | WO 2009/120767 A1 | 10/2009 |
| WO | WO 2011/050103 A1 | 4/2011 |
| WO | WO 2011/093927 A1 | 8/2011 |
| WO | WO 2012/103025 A2 | 8/2012 |
| WO | WO 2013/049926 A1 | 4/2013 |
| WO | WO 2013/086428 A1 | 6/2013 |
| WO | WO 2013/111054 A1 | 8/2013 |
| WO | WO 2013/181532 A1 | 12/2013 |
| WO | WO 2014/008155 A1 | 1/2014 |
| WO | WO 2014/066864 A2 | 5/2014 |
| WO | WO 2014/120265 A1 | 8/2014 |
| WO | WO 2014/151006 A2 | 9/2014 |
| WO | WO 2015/048740 A1 | 4/2015 |
| WO | WO 2015/112955 A1 | 7/2015 |
| WO | WO 2015/112999 A1 | 7/2015 |
| WO | WO 2015/116828 A1 | 8/2015 |

OTHER PUBLICATIONS

Alix-Panabières et al., "Circulating tumor cells and circulating tumor DNA," *Annu. Rev. Med.*, 63:199-215 (2012).

Alix-Panabières et al., "Circulating tumor cells: liquid biopsy of cancer," *Clin. Chem.*, 59(1):110-118 (2013).

Allard et al., "Tumor cells circulate in the peripheral blood of all major carcinomas but not in healthy subjects or patients with nonmalignant diseases," *Clin. Cancer Res.*, 10(20):6897-6904 (2004).

Amato et al., "Epithelial cell adhesion molecule-positive circulating tumor cells as predictive biomarker in patients with prostate cancer," *Urology*, 81(6):1303-1307 (2013).

Angerer et al., "Demonstration of tissue-specific gene expression by in situ hybridization," *Methods Enzymol.*, 152:649-661 (1987).

Antonarakis et al., "AR-V7 and resistance to enzalutamide and abiraterone in prostate cancer," *N. Engl. J. Med.*, 371(11):1028-1038 (2014).

Aparico et al., "Platinum-based chemotherapy for variant castrate-resistant prostate cancer," *Clin. Cancer Res.*, 19(13):3621-3630 (2013).

Armstrong et al., "Biomarkers in the management and treatment of men with metastatic castration-resistant prostate cancer," *Eur. Urol.*, 61(3):549-559 (2012).

Arya et al., "Enrichment, detection and clinical significance of circulating tumor cells," *Lab. Chip.*, 13(11):1995-2027 (2013).

Asworth, "A case of cancer in which cells similar to those in the tumours were seen in the blood after death," *Australian Med. J.*, 14: 146-147 (1869).

Attard et al., "Characterization of ERG, AR and PTEN gene status in circulating tumor cells from patients with castration-resistant prostate cancer," *Cancer Res.*, 69(7):2912-2918 (2009).

Autio et al., "Heterogeneity of prostate-specific membrane antigen expression in traditional and apoptotic circulating tumor cells in metastatic castration-resistant prostate cancer," American Society of Clinical Oncology Genitourinary (ASCO GU) conference, Jan. 30, 2014, San Francisco, CA, J. Clin. Oncol., 32(4):Abstract 198 (2014).

Balic et al., "Circulating tumor cells: from bench to bedside," *Annu. Rev. Med.*, 63:31-44 (2013).

Balic et al., "Progress in circulating tumor cell capture and analysis: implications for cancer management," *Expert Rev. Mol. Diagn.*, 12(3):303-312 (2012).

Beltran et al., "Aggressive variants of castration-resistant prostate cancer," *Clin. Cancer Res.*, 20(11):2846-2850 (2014).

Beltran et al., "Challenges in recognizing treatment-related neuroendocrine prostate cancer," *J. Clin. Oncl.*, 30(36):e386-e389 (2012).

Beltran et al., "Molecular characterization of circulating tumor cells of patients with neuroendocrine prostate cancer," American Society of Clinical Oncology Genitourinary (ASCO GU) conference, Jan. 30, 2014, San Francisco, CA, J. Clin. Oncol., 32(4):Abstract 177 (2014).

Beltran et al., "Molecular characterization of neuroendocrine prostate cancer and identification of new drug targets," *Cancer Discov.*, 1(6):487-495 (2011).

Beltran et al., "New strategies in prostate cancer: translating genomics into the clinic," *Clin. Cancer Res.*, 19(3):517-523 (2013).

Bovee et al., "Loss of heterozygosity and DNA ploidy point to a diverging genetic mechanism in the origin of peripheral and central chondrosarcoma," *Genes, Chromosomes & Cancer*, 26:237-246 (1999).

Box et al., "An analysis of transformations," *J. Royal Statist. Soc.*, Series B, 26(2):211-243 (1964).

Brandt et al., "Isolation of prostate-derived single cells and cell clusters from human peripheral blood," *Cancer Res.*, 56(20):4556-4561 (1996).

Breiman, "Random Forests," *Machine Learning*, 45:5-32 (2001).

Brenner et al., "ETS Fusion Genes in Prostate Cancer," *Prostate Cancer: Biochemistry, Molecular Biology and Genetics*, Tindall ed., Springer, New York, 16:139-183 (2013).

Chan et al., "Dramatically elevated circulating tumor cell numbers in a patient with small cell neuroendocrine carcinoma of the prostate," *Arch. Pathol. Lab. Med.*, 134(1):120-123 (2010).

Chang et al., "High-risk prostate cancer-classification and therapy," *Nat. Rev. Clin. Oncol.*, 11(6):308-323 (2014).

Chinen et al., "Cytokeratin-based CTC counting unrelated to clinical follow up," *J. Thorac. Dis.*, 5(5):593-599 (2013).

(56) References Cited

OTHER PUBLICATIONS

Cho et al., "Characterization of circulating tumor cell aggregates identified in patients with epithelial tumors," *Phys. Biol.*, 9:016001 (2012).
Cohen et al., "Prognostic significance of circulating tumor cells in patients with metastatic colorectal cancer," *Ann. Oncol.*, 20(7):1223-1229 (2009).
Cohen et al., "Relationship of circulating tumor cells to tumor response, progression-free survival, and overall survival in patients with metastatic colorectal cancer," *J. Clin. Oncol.*, 26(19):3213-3221 (2008).
Cookson et al., "Castration-resistant prostate cancer: AUA Guideline," *J. Urol.*, 190(2):429-438 (2013).
Cristofanilli et al., "Circulating tumor cells, disease progression, and survival in metastic breast cancer," *N. Engl. J. Med.*, 351(8):781-791 (2004).
Cristofanilli et al., "Circulating tumor cells: a novel prognostic factor for newly diagnosed metastatic breast cancer," *J. Clin. Oncol.*, 23(7): 1420-1430 (2005).
Cristofanilli, "The biological information obtainable from circulating tumor cells," *Breast*, 3:S38-S40 (2009).
Curry et al., "High-speed detection of occult tumor cells in peripheral blood," *Proceedings of the 26th Annual International Conference of the IEEE EMBS*, San Francisco, CA USA, Sep. 1-5, pp. 1267-1270 (2004).
Damani et al., "Characterization of circulating endothelial cells in acute myocardial infarction," *Sci. Tranl. Med.*, 4(126):126ra33 (2012).
Danila et al., "TMPRSS2-ERG status in circulating tumor cells as a predictive biomarker of sensitivity in castration-resistant prostate cancer patients treated with abiraterone acetate," Eur. Urol., 60(5):897-904 (2011).
Danila et al., "Circulating tumor cell number and prognosis in progressive castration-resistant prostate cancer," *Clin. Cancer Res.*, 13(23):7053-7058 (2007).
Danila et al., "Circulating tumors cells as biomarkers: progress toward biomarker qualification," *Cancer J.*, 17(6):438-450 (2011).
De Bono et al., "Circutlating tumor cells predict survival benefit from treatmetn in metastatic castration-resistant prostate cancer," *Clin. Cancer Res.*,14(19):6302-6309 (2008).
De Giorgi et al., "Application of a filtrationo- and isolation-by-size technique for the detection of circulating tumor cells in cutaneous melanoma," *J. Invest. Dermatol.*, 130:2440-2447 (2010).
Diamond et al., "Isolation and characterization of circulating tumor cells in prostate cancer," *Front Oncol.*, 2:131 (2012).
Dittamore et al., "Molecuar characterization of circulating tumor cells (CTCs) and CTC subpopulations in progressive metastatic castration-restitant prostate cancer (mCRPC)," American Society of Clinical Oncology Genitourinary (ASCO GU) conference, Jan. 30, 2014, San Francisco, CA, J. Clin. Oncol., 32(4):Abstract 132 (2014).
European Search Report (ESR) from application No. EP 10825626, dated Apr. 18, 2013.
Fehm et al., "Methods for isolating circulating epithelial cells and criteria for their classification as carcinoma cells," *Cytotherapy*, 7(2):171-185 (2005).
Ferraldeschi et al., "CK- and small nuclear size circulating tumor cell phenotypes in metastatic castration-resistant prostate cancer," American Society of Clinical Oncology Genitourinary (ASCO GU) conference, Jan. 30, 2014, San Francisco, CA, J. Clin. Oncol., 32(4):Abstract 209 (2014).
Gazzaniga et al., "Circulating tumor cells: highlight on practical implications," *Mol. Diagn. Ther.*, 16(1):7-11 (2012).
Giordano et al., "Epithelial-mesenchymal transition and stem cell markers in patients with HER2-positive metastatic breast cancer," *Mol. Cancer Ther.*, 11(11):2526-2534 (2012).
Gorges et al., "Circulating tumor cells as therapy-related biomarkers in cancer patients," *Cancer Immunol. Immunother.*,62(5):931-939 (2013).
Gorges et al., "Circulating tumour cells escape from EpCAM-based detection due to epithelial-to-mesenchymal transition," *BMC Cancer*, 12:178 (2012).
Grasso et al., "The mutational landscape of lethal castration-resistant prostate cancer," *Nature*, 287(7406):239-243 (2012).
Guo et al., "A new trick of an old molecule: androgen receptor splice variants taking the stage?!," Int. J. Bio. Sci., 7(6):815-822 (2011).
Hager et al., "The use of a panel of monoclonal antibodies to enrich circulating breast cancer cells facilitates their detection," *Gynecol. Oncol.*, 98(2):211-216 (2005).
Hanash et al., "Mining the plasma proteome for cancer biomarkers," *Nature*, 452(7187):571-579 (2008).
Hofman et al., "Preoperative circulating tumor cell detection using the isolation by size of epithelial tumor cell method for patients with lung cancer is a new prognostic biomarker," 17(4):827-835 (2011).
Hou et al., "Isolation and retrieval of cirulating tumor cells using centrifugal forces," *Scientific Reports*, 3(1259):1-8 (2013).
Hsieh et al., "High speed detection of circulating tumor cells," *Biosens. Bioectron.*, 21:1893-1899 (2006).
Ignatiadis et al., "Prognostic value of the molecular detection of circulating tumor cells using a multimarker reverse transcription-PCR assay for cytokeratin 19, mammaglobin A, and HER2 in early breast cancer," *Clin. Cancer Res.*, 14(9):2593-2600 (2008).
Ihaka et al., "A langauge for data analysis and graphics," *J. Comput. Graph. Statist.*, 5(3):299-314 (2012).
Ioannidis, "Why most published research findings are false," *PLoS Med.*, 2(8):e124 (2005).
Jiang et al., "Detection of androgen receptor mutations in circulating tumor cells in castration-resistant prostate cancer," Clin. Chem., 56(9):1492-1495 (2010).
Jilaveanu et al., "PD-L1 expression in clear cell renal cell carcinoma: an analysis of nephrectomy and sites of metastases," J. Cancer, 5(3):166-172 (2014).
Jones et al., "Wright-Giemsa cytology of body fluids," *Laboratory Medicine*, 28(11):713-716 (1997).
Joosse et al., "Biologic challenges in the detection of circulating tumor cells," *Cancer Res.*, 73(1):8-11 (2013).
Jung et al., "Fluorescence quenching of green fluorescent protein during denaturation by guanidine," *Bull.Korean Chem. Soc.*, 26(3):413-417 (2005).
Kalluri et al., "The basics of epithelial-mesenchymal transition," *J. Clin. Invest.*, 119(6):1420-1428 (2009).
Kang et al., "A combined micromagnetic-microfluidic device for rapid capture and culture of rare circulating tumor cells," *Lab. Chip.*, 12:2175-2181 (2012).
Kodiha et al., "Computer-based fluorescence quantification: a novel approach to study nucleolar biology," BMC Cell Biol., 12:25, 1-18 (2011).
Kolatkar et al., "C-ME: a 3D community-based, real-time collaboration tool for scientific research and training," *PLoS One*, 3(2):e1621 (2008).
Kraeft et al., "Detection and analysis of cancer cells in blood and bone marrow using a rare event imaging system," Clin. Cancer Res., 6:434-442 (2000).
Kraeft et al., "Detection and analysis of lung cancer cells from body fluids using a rare event imaging system," *Methods Mol. Med.*, 75:423-430 (2003).
Kraeft et al., "Reliable and sensitive identification of occult tumor cells using the improved rare event imaging system," *Clin. Cancer Res.*, 10(9):3020-3028 (2004).
Krebs et al., "Evaluation and prognostic significance of circulating tumor cells in patients with non-small-cell lung cancer," *J. Clin. Oncol.*, 29(12): 1556-1563 (2011).
Krebs et al., "Molecular analysis of circulating tumour cells-biology and biomarkers," *Nat. Rev. Clin. Oncol.*, 11(3):129-144 (2014).
Krivacic et al., "A rare-cell detector for cancer," *Proc. Natl. Acad. Sci. USA*, 101(29):10501-10504 (2004).
Kuhn et al., "A fluid biopsy as investigating technology for the fluid phase of solid tumors," *Phys. Biol.*, 9(1): 010301 (2012).
Leversha et al., "Fluorescence in situ hybridization analysis of circulating tumor cells in metastatic prostate cancer," Clin. Cancer Res., 15:2091-2097 (2009).

(56) References Cited

OTHER PUBLICATIONS

Ligthart et al., "Unbiased and automated identification of a circulating tumour cell definition that associates with overall survival," PLoS One, 6(11):e27419 (2011).
Lin et al., "Disseminated and circulating tumor cells: Role in effective cancer management," Crit. Rev. Oncol. Hematol., 77(1):1-11 (2011).
Lin et al., "Portable filter-based microdevice for detection and characterization of circulating tumor cells," Clin. Cancer Res., 16(20):5011-5018 (2010).
Liotta et al., "The significance of hematogenous tumor cell clumps in the metastatic process," Cancer Res., 36(3):889-894 (1976).
Lu et al., "Parylene membrane slot filter for the capture, analysis and culture of viable circulating tumor cells," IEEE 23rd International Conferernce, Piscataway, NJ, Jan. 24, 2010, pp. 935-938.
Lucci et al., "Circulating tumour cells in non-metastatic breast cancer: a prospective study," Lancet Oncol., 13(7):688-695 (2012).
Maheswaran et al., "Detection of mutations in EGFR in circulating lung-cancer cells," N. Eng. J. Med., 359(4):366-377 (2008).
Marrinucci et al., "Bronchioloalveolar lung CTCs retain cytomorphologic features of primary tumor type," J. Clin. Oncol., 26(15S):19118 (2008).
Marrinucci et al., "Case study of the morphologic variation of circulating tumor cells," Hum. Pathol., 38(3):514-519 (2006).
Marrinucci et al., "Circulating tumor cells from well-differentiated lung adenocarcinoma retain cytomorphologic features of primary tumor type," Arch. Pathol. Lab. Med., 133(9):1468-1471 (2009).
Marrinucci et al., "Cytomorphology of circulating colorectal tumor cells:a small case series," J. Oncol., 2010:861341 (2010).
Marrinucci et al., "Fluid biopsy in patients with metastatic prostate, pancreatic and breast cancers," Phys. Biol., 9(1):016003 (2012) abstract.
Mateo et al., "The promise of circulating tumor cell analysis in cancer management," Genome Biol., 15(8):448 (2014).
Meng et al., "Circulating tumor cells in patients with breast cancer dormancy," Clin. Cancer Res., 10(24):8152-8162 (2004).
Mezynski et al., "Antitumour activity of docetaxel following treatment with the CYP17A1 inhibitor abiraterone: clinical evidence for cross-resistance?," Ann. Oncol., 23(11):2943-2947 (2012).
Miller et al., "Significance of circulating tumor cells detected by the CellSearch System in patients with metastatic breast colorectal and prostate cancer," J. Oncol., 2010:617421 (2010).
Miyake et al., "Alpha-fetoprotein and human chorionic gonadotropin-producing lung cancer," Cancer; 59(2):227-232 (1987).
Miyamoto et al., "Androgen receptor signaling in circulating tumor cells as a marker of hormonally responsive prostate cancer," Cancer Discov., 2(11):995-1003 (2012).
Mohler et al., "Prostate cancer, version 1.2014," J. Natl. Compr. Canc. Netw., 11(12):1471-1479 (2013).
Mohler et al., "Prostate cancer, version 2.2014," J. Natl. Compr. Canc. Netw., 12(5):686-718 (2014).
Molnar et al., "Circulating tumor cells clusters in the peripheral blood of colorectal cancer patients," Clin. Cancer Res., 7(12):4080-4085 (2001).
Mosquera et al., "Concurrent AURKA and MYCN gene amplifications are harbingers of lethal treatment-related neuroendocrine prostate cancer," Neoplasia, 15(1):1-10 (2013).
Mostaghel et al., "Molecular pathways: targeting resistance in the androgen receptor for therapeutic benefit," Clin. Cancer Res., 20(4):791-798 (2014).
Nagle et al., "ERG overexpression and PTEN status predict capsular penetration in prostate carcinoma," Prostate, 73(11):1233-1240 (2013).
Nagrath et al., "Isolation of rare circulating tumour cells in cancer patients by microchip technology," Nature, 450(7173):1235-1239 (2007).
Nair et al., "An observational study of circulating tumor cells and $^{18}$F-FDG PET uptake in patients with treatment-naive non-small cell lung cancer," PLoS One, 8(7):e67733 (2013).

Nair et al., "Clinical outcome prediction by microRNAs in human cancer: a systematic review," J. Natl. Cancer Inst., 104(7): 528-540 (2012).
Nieva et al., "High-definition imaging of circulating tumor cells and associated cellular events in non-small cell lung cancer patients: a longitudinal analysis," Phys. Biol., 9(1):016004 (2012).
Noonan et al., "Clinical activity of abiraterone acetate in patients with metastatic castration-resistant prostate cancer progressing after enzalutamide," Ann. Oncol., JD 24(7):1802-1807 (2013).
Olmos et al., "Circulating tumour cell (CTC) counts as intermediate end points in castration-resistant prostate cancer (CRPC): a single-centre experience," Ann. Oncol., 20(1):27-33 (2009).
Ozkumur et al., "Inertial focusing for tumor antigen-dependent and -independent sorting of rare circulating tumor cells," Sci. Transl. Med., 5(179):179ra47 (2013).
Pantel et al., "Circulating epithelial cells in patients with benign colon diseases," Clin. Chem., 58(5):936-940 (2012).
Pantel et al., "The potential of circulating tumor cells as a liquid biopsy to guide therapy in prostate cancer," Cancer Discov.,2(11):974-975 (2012).
Park et al., "Highly efficient assay of circulating tumor cells by selective sedimentation with a density gradient medium and microfiltration from whole blood," Anal. Chem., 84:7400-7407 (2012).
Park et al., "Morphological differences between circulating tumor cells from prostate cancer patients and cultured prostate cancer cells," PLoS One, 9(1):e85264 (2014).
Parkinson et al., "Considerations in the development of circulating tumor cell technology for clinical use," J. Transl., Med., 10:138 (2012).
Pecot et al., "A novel platform for detection of CK+and CK–CTCs," Cancer Discov., 1(7):580-586 (2011).
Pezaro et al., "Activity of cabazitaxel in castration-resistant prostate cancer progressing after docetaxel and next-generation endocrine agents," Eur. Urol., 66(3):459-465 (2014).
Phillips et al., "Physical biology in cancer. 2. The physical biology of circulating tumor cells," Am. J. Physiol. Cell Physiol., 306(2):C80-C88 (2014).
Picard et al., "Cross-validation of regression models," J. Am. Statist. Assoc., 79(387):575-583 (1984).
Pierga et al., "High independent prognostic and predictive value of circulating tumor cells compared with serum tumor markers in a large prospective trial in first-line chemotherapy for metastatic breast cancer patients," Annals. Oncol., 23:618-624 (2012).
Polzer et al., "Molecular profiling of single circulating tumor cells with diagnostic intention," EMBO Mol. Med., 6(11):1371-1386 (2014).
Punnoose et al., "Evaluation of circulating tumor cells and circulating tumor DNA in non-small cell lung cancer: association with clincal endpoints in a phase II clinical trial of pertuzumab and erlotinib," Clin. Cancer Res., 18(8):1-11 (2012).
Qimaging, User Manual Retiga™ EXi FAST1394 (2003).
Rami-Porta et al., "The IASLC Lung Cancer Staging Project: proposals for the revision of the T descriptors in the forthcoming (seventh) edition of the TNM classification for lung cancer," J. Thorac. Oncol., 2(7):593-602 (2007).
Reyal et al., "Circulating tumor cell detection and transcriptomic profiles in early breast cancer patients," Ann. Oncol., 22(6):1458-1459 (2011).
Reyes et al., "Quantitative characterization of androgen receptor protein expression and cellular localization in circulating tumor cells from patients with metastatic castration-resistant prostate cancer," J. Transl. Med., 12(1):313 (2014).
Rickman et al., "ERG cooperates with androgen receptor in regulating trefoil factor 3 in prostate cancer disease progression," Neoplasia,12(12):1031-1040 (2010).
Romsdahl et al., "The time of metastasis and release of circulating tumor cells as determined in an experimental system," Cancer, 14:883-888 (1961).
Roudier et al., "Phenotypic heterogeneity of end-stage prostate carcinoma metastatic to bone," Hum. Pathol., 34(7):646-653 (2003).
Santoni et al., "Neuroendocrine differentiation in prostate cancer: novel morphological insights and future therapeutic perspectives," Biochim. Biophys. Acta., 1846(2):630-637 (2014).

(56) References Cited

OTHER PUBLICATIONS

Scheel et al., "Cancer stem cells and epithelial-mesenchymal transition: concepts and molecular links," Semin. Cancer Biol., 22(5-6):396-403 (2012).
Scher et al., "Circulating tumour cells as prognostic markers in progressive, castration-resistant prostate cancer: a reanalysis of IMMC38 trial data," Lancet Oncol., 10(3):233-239 (2009).
Schreuder, "Laser image cytometer for analysis of circulating tumor cells," Ph.D. diss., 153 pp., (2008), Universiteit Twente, Zutphen, The Netherlands.
Schultz et al., "Validation of two models to estimate the probability of malignancy in patients with solitary pulmonary nodules," Thorax, 63(4):335-341 (2008).
Scotton et al., "Epithelial cancer cell migration: a role for chemokine receptors?," Cancer Res., 61(13):4961-4965 (2001).
Self et al., "Advances in immunoassay technology," Curr. Opin. Biotchnol., 7(1):60-65 (1996).
Shah et al., "Androgen-independent prostate cancer is a heterogeneous group of diseases: lessons from a rapid autopsy program," Cancer Res., 64(24):9209-9216 (2004).
Shankar et al., "Consensus recommendations for the use of $^{18}$F-FDG PET as an indicator of therapeutic response in patients in National Cancer Institute Trials," J. Nucl. Med., 47(6):1059-1066 (2006).
Siegel et al., "Cancer statistics, 2014," CA Cancer J. Clin.,64(1):9-29 (2014).
Somlo et al., "Multiple biomarker expression on circulating tumor cells in comparison to tumor tissues from primary and metastic sites in patients with locally advanced/inflammatory, and stage IV breast cancer, using a novel detection technology," Breast Cancer Res. Treat., 128(1):155-163 (2011).
Stanbrough et al., "Prostatic intraepithelial neoplasia in mice expressing an androgen receptor transgene in prostate epithelium," Proc. Natl. Acad. Sci USA, 98(19):10823-10828 (2001).
Stepanenko et al., "Distinct effects of guanidine thiocyanate on the structure of superfolder GFP," PLoS One, 7(11):e48809 (2012).
Stott et al., "Isolation of circulating tumor cells using a microvortex-generating herringbone-chip," Proc. Natl. Acad. Sci. USA, 107(43):18392-18397 (2010).
Stott et al., "Isolation and characterization of circulating tumor cells from patients with localized and metastic prostate cancer," Sci. Transl. Med., 2(25):25ra23 (2010).
Tagawa, "Neuroendocrine prostate cancer after hormonal therapy: knowing is half the battle," J. Clin. Oncol., 32(30):3360-3364 (2014).
Takahashi, "An experimental study of metastasis," J. Path. Bacter., 20(1): 1-13 (1915).
Tanaka et al., "Circulating tumor cell as a diagnostic marker in primary lung cancer," Clin. Cancer Res., 15(22):6980-6986 (2009).
Tanaka et al., "Circulating tumor cells (CTCs) in lung cancer: current status and future perspectives," Lung Cancer: Targets and Therapy, 1:77-84 (2010).
Tibshirani, "Regression skrinkage and selection via the lasso," J. Royal Statist Soc., Series B, 58(1):267-288 (1996).
Vincent et al., "Carcinoembryonic antigen in 228 patients with carcinoma of the lung," Cancer, 36(6):2069-2076 (1975).
Vona et al., "Enrichment, immunomorphological, and genetic characterization of fetal cells circulating in maternal blood," Am. J. Pathol.,160(1):51-58 (2002).
Vona et al., "Isolation by size of epithelial tumor cells: a new method for the immunomorphological and molecular characterization of circulatingtumor cells," Am. J. Pathol., 156(1):57-63 (2000).
Watanabe et al., "Multicolor detection of rare tumor cells in blood using a novel flow cytometry-based system," CytometryA., 85(3):206-213 (2014).
Waters, "Accuracy and precision in quantitative fluorescence microscopy," J. Cell Biol., 185(7):1135-1148 (2009).
Witzig et al., "Detection of circulating cytokeratin-positive cells in the blood of breast cancer patients using immunomagnetic enrichment and digital microscopy," Clin. Cancer Res., 8(5):1085-1091 (2002).
Yap et al., "Circulating tumor cells: a multifunctional biomarker," Clin. Cancer Res., 20(10):2553-2568 (2014).
Yu et al., "Circulating tumor cells: approaches to isolation and the characterization," J. Cell Biol., 192(3):373-382 (2011).
Yu et al., "Circulating breast tumor cells exhibit dynamic changes in epithelial and mesenchymal composition," Science, 339(6119):580-584 (2013).
Zhang et al., "Androgen receptor variants occur frequently in castration resistant prostate cancer metastases," PLoS One, 6(11):e27970 (2011).
Zhang et al., "The identification and characterization of breast cancer CTCs competent for brain metastasis," Sci. Transl. Med., 5(180):180ra48 (2013).
Zheng et al., "Level of circulating PD-L1 expression in patients with advanced gastric cancer and its clinical implications," Chin. J. Cancer Res., 26(1):104-111 (2014).
Zheng et al., "Membrane microfilter device for selective capture, electrolysis and genomic analysis of human circulating tumor cells," J. Chromatogr., 1162(2):154-161 (2007).
Borgen et al., "Use of automated microscopy for the deteection of disseminated tumor cells in bone marrow samples," Cytometry, 46:215-221 (2001).
Mohamed et al., "Isolation of tumor cells using size and deformation," J. Chromatogr. A., 1216(47):8289-8295 (2009).
Theodoropoulo et al., "Circulating tumor cells with a putative stem cell phenotype in peripheral blood of patients with breast cancer," Cancer Letts., 288:99-106 (2010).
Abkevich et al., "Patterns of genomic loss of heterozygosity predict homologous recombination repair defects in epithelial ovarian cancer," Br. J. Cancer, 107(10):1776-1782 (2012).
Anonymous, "Circulating tumor cell," Wikipepia, Jan. 13, 2015, retrieved from the internet: URL:https://en.wikipedia.org/w/index.php?title=Circulating_tumor_cell&oldid=642235295 [retrieved on May 3, 2018], 14 pages.
Antonarakis et al., "Androgen Receptor Splice Variant 7 and Efficacy of Taxane Chemotherapy in Patients With Metastatic Castration-Resistant Prostate Cancer," JAMA Oncol., 1(5):582-591 (2015).
Antonarakis et al., "AR splice variant (AR-V7) and response to taxanes in men with metastatic castration-resistant prostate cancer (mCRPC)," J. Clin. Oncol., 33(Suppl 7):138 (2015). Abstract only.
Ariosa Diagnostics Center, Inc. v. Sequenom, Inc., Opinion of the United States Court of Appeals for the Federal Circuit, pp. 1-21 (2015).
Armstrong et al., "Circulating tumor cells from patients with advanced prostate and breast cancer display both epithelial and mesenchymal markers," Mol. Cancer Res., 9(8):997-1007 (2011).
Arora et al., "Glucocorticoid receptor confers resistance to antiandrogens by bypassing androgen receptor blockade," Cell, 155(6):1309-1322 (2013).
Attard et al, "Utilizing circulating tumor cells: challenges and pitfalls," Curr. Opin. Gen. Dev., 21:50-58 (2011).
Attard et al., "Selective inhibition of CYP17 with abiraterone acetate is highly active in the treatment of castration-resistant prostate cancer," J. Clin. Oncol.,27(23):3742-3748 (2009).
Balmana et al., "Phase I trial of olaparib in combination with cisplatin for the treatment of patients with advanced breast, ovarian and other solid tumors," Ann. Oncol., 25(8):1656-1663 (2014).
Bambury et al., "Characteristics of de novo reistance to androgen targeting therapeutics (AR TX) through circulating tumor cells (CTCS) analysis in metastatic castration resistant prostate cancer (MCRPC) patients," Annals. Oncol., 25(Suppl. 4):iv58-iv84, Abstract 237P (2014).
Becker et al., "New frontiers in circulating tumor cell analysis: A reference guide for biomolecular profiling toward translational clinical use," Int. J. Cancer, 134(11):2523-2533 (2014).
Beltran et al., "The initial detection and partial characterization of circulating tumor cells in neuroendocrine prostate cancer," Clin. Cancer Res., 22(6):1510-1519 (2016).

(56) References Cited

OTHER PUBLICATIONS

Brenner et al., "Gene expression analysis by massively parallel signature sequencing (MPSS) on microbead arrays," *Nat. Biotechnol.*, 18(6):630-634 (2000).
Chang, "Treatment options for hormone-refractory prostate cancer," *Rev. Urol.*, 9(Suppl 2):S13-S18 (2007).
Chen et al., "Clinical significance of programmed death-1 ligand-1 expression in patients with non-small cell lung cancer: a 5-year-follow-up study," *Tumori*, 98(6):751-755 (2012) Abstract only.
Cloonan et al., "Stem cell transcriptome profiling via massive-scale mRNA sequencing," *Nat. Methods*,5(7):613-619 (2008).
Darshan et al., "Taxane-induced blockade to nuclear accumulation of the androgen receptor predicts clinical responses in metastatic prostate cancer," *Cancer Res.*, 71(18):6019-6029 (2011).
Del Conte et al., "Phase I study of olaparib in combination with liposomal doxorubicin in patients with advanced solid tumours," *Br. J. Cancer*, 111(4):651-659 (2014).
Etzioni et al., "The case for early detection," *Nature Rev.*, 3:1-10 (2003).
Evans et al., "Noninvasive measurement of androgen receptor signaling with a positron-emitting radiopharmaceutical that targets prostate-specific membrane antigen," *Proc. Natl. Acad. Sci. USA*, 108(23):9578-9582 (2011).
Friedlander et al., "Detection and genomic interrogation of circulating tumor cells (CTCs) and circulating tumor stem cells (CTSCs) from men with metastatic castration-resistant prostate cancer (mCRPC)," *Eur. J. Cancer*, 48(Supp 6):152, Abstract 490 (2012).
Gibbs et al., "Abstract 4816: Development of an integrated analysis platform of circulating melanoma cells for PD-L1 expression as a predictive biomarker," *Cancer Res.*, 74(19 Suppl):Abstract 4816 (2014).
Giuliano et al., "Circulating tumor cells as early predictors of metastatic spread in breast cancer patients with limited metastatic dissemination," *Breast Cancer Res.*, 16(5):440 (2014).
Gross et al., "Abstract 3630: Non-enrichment based method for analysis of androgen receptor expression in circulating tumor cells (CTCs) in patients with metastatic castrate resistant prostate cancer," Proceedings: AACR 103rd Annual Meeting, Chicago, IL Mar. 31-Apr. 4, 2012, Retrieved from the Internet: URL:http://cancerres.aacrjournals.org/content/72/8_Supplement/3630 [retrieved on Jun. 13, 2017], 3 pages.
Guo et al., "A novel androgen receptor splice variant is up-regulated during prostate cancer progression and promotes androgen depletion-resistant growth," *Cancer Res.*, 69(6):2305-2313 (2009).
Hao et al., "In vitro and in vivo prostate cancer metastasis and chemoresistance can be modulated by expression of either CD44 and CD147," *PLoS One*, 7(8):e40716 (2012).
Harada et al., "Androgen deprivation causes truncation of the C-terminal region of androgen receptor in human prostate cancer LNCaP cells," *Cancer Sci.*, 103:1022-1027 (2012).
Isakoff et al., "TBCRC009: A Multicenter Phase II Clinical Trial of Platinum Monotherapy With Biomarker Assessment in Metastatic Triple-Negative Breast Cancer," *J. Clin. Oncol.*, 33(17):1902-1909 (2015).
Jiang et al., "A comparison of isolated circulating tumor cells and tissue biopsies using whole-genome sequencing in prostate cancer," Oncotarget, 6(42):44781-44793 (2015).
Kraan et al., "A new approach for rapid and reliable enumeration of circulating endothelial cells in patients," *J. Thromb. Haemost.*, 10(5):931-939 (2012).
Krebs et al., "Analysis of circulating tumor cells in patients with non-small cell lung cancer using epithelial marker-dependent and -independent approaches," *J. Thorac Oncol.*, 7:306-315 (2012).
Kryzwinski et al., "Circos: an information aesthetic for comparative genomics," *Genome Res.*, 19(9):1639-1645 (2009).
Larson et al., "Apoptosis of circulating tumor cells in prostate cancer patients," *Cytometry*, 62A:46-53 (2004).
Li et al., "Detection and validation of circulating endothelial cells, a blood-based diagnostic marker of acute myocardial infarction," *PLoS One*, 8(3):e58478 (2013).
Libertini et al., "Evidence for calpain-mediated androgen receptor cleavage as a mechanism for androgen independence," *Cancer Res.*, 67(19):9001-9005 (2007).
Lin et al., "A negative selection system PowerMag for effective leukocyte depletion and enhanced detection of EpCAM positive and negative circulating tumor cells," *Clinica Chem Acta*, 419:77-84(2013).
Ma et al., "Potent antitumor activity of an auristatin-conjugated, fully human monoclonal antibody to prostate-specific membrane antigen," *Clin. Cancer Res.*, 12(8):2591-2596 (2006).
Marioni et al., "RNA-seq: an assessment of technical reproducibility and comparison with gene expression arrays," *Genome Res.*, 18(9):1509-1517 (2008).
Marquard et al., "Pan-cancer analysis of genomic scar signatures associated with homologous recombination deficiency suggests novel indications for existing cancer drugs," *Biomark Res.*, 3:9 (2015).
Mateo et al., "DNA-repair defects and olaparib in metastatic prostate cancer," *N. Engl. J. Med.*, 373(18):1697-1708 (2015).
Mcdaniel et al., "Phenotypic diversity of circulating tumour cells in patients with metastatic castration-resistant prostate cancer," *BJU Int.*, 120(5B):E30-E44 (2017).
Melnikova et al., "Molecular characterizatoin of circulating tumor cells using a highly sensitive method of enrichment based on the CellSearch CTC profile kit," 22nd EORTC-NCI-AACR Symposium on Molecular Targets and Cancer; poster session, Jan. 1, 2010 (1 page).
Mikolajczyk et al., "Detection of EpCAM-negative and cytokeratin-negative circulating tumor cells in peripheral blood," *J. Oncol.*, 2011:252361, 10 pages (2011).
Miyamoto et al., "Androgen receptor signaling in circulating tumor cells as a marker of hormonally responsive prostate cancer: supplemental methods single molecule sequencing and AR transcriptional signature," Retrieved from the internet: URL:http://http://cancerdiscovery.aacrjournals.org/content/suppl/2012/09/14/2159-8290.CD-12-0222.DC1. [retrieved on Apr. 16, 2019] DOI: 10.1158/2159-8290.CD-12-0222 (2012).
Morin et al., "Application of massively parallel sequencing to microRNA profiling and discovery in human embryonic stem cells," *Genome Res.*, 18(4):610-621 (2008).
Morrison et al., "Labeling fluorescence in situ hybridization probes for genomic targets," in *Molecular Cytogenetics: Protocols and Applications*, Y.S. Fan Ed., Humana Press, Chapter 2, pp. 21-40 (2002).
Mortazavi et al., "Mapping and quantifying mammalian transcriptomes by RNA-Seq," *Nat. Methods*, 5(7):621-628 (2008).
Mumford et al., "Circulating melanoma cells in the diagnosis and monitoring of melanoma: an appraisal of clinical potential," *Mol. Diang. Ther.*, 18(2):175-183 (2014).
Nagy et al., "Mulitiplexed protein and gene profiling of circulating tumor cells (CTCs) in metastatic castration-resistant prostate cancer (mCRPC) using automated immunofluorescence and fluorescence in situ hybridization," *J. Clin. Oncol.*, 31(6):Suppl. 1, Abstract No. 158, (2013).
Paterlini-Brechot et al., "Circulating tumor cells (CTC) detection: clinical impact and future directions," *Cancer Lett.*, 253:180-204 (2007).
Pestana et al., Improved diffuse fluorescence flow cytometer prototype for high sensitivity detection of rare circulating cells in vivo, *J. Biomed. Optics*, 18(7):077002 (2013).
Popova et al., "Ploidy and large-scale genomic instability consistently identify basal-like breast carcinomas with BRCA1/2 inactivation," *Cancer Res.*, 72(21):5454-5462 (2012).
Punnoose et al., "PTEN loss in circulating tumour cells correlates with PTEN loss in fresh tumour tissue from castration-resistant prostate cancer patients," *Br. J. Cancer*, 113(8):1225-1233 (2015).
Racila et al., "Detection and characterization of carcinoma cells in the blood," *Proc. Natl. Acad. Sci. USA*, 95(8):4589-4594 (1998).
Rathkopf et al., "Androgen receptor antagonists in castration-resistant prostate cancer," *Cancer J.*, 19(1):43-49 (2013).
Ren et al., "Detection of apoptotic circulating tumor cells in advanced pancreatic cancer following 5-fluorouracil chemotherapy," *Cancer Biol. Ther.*, 12(8):700-706 (2011).

(56) References Cited

OTHER PUBLICATIONS

Riethdorf et al., "Detection of circtulating tumor cells in peripheral blood of patients with metastatic breast cancer: a validation study of the CellSearch System," *Clin. Cancer Res.*, 13(3):920-928 (2007).
Robinson et al., "Integrative clinical genomics of advanced prostate cancer," *Cell*, 161(5):1215-1228 (2015).
Scher et al., "Association of AR-V7 on Circulating Tumor Cells as a Treatment-Specific Biomarker With Outcomes and Survival in Castration-Resistant Prostate Cancer," *JAMA Oncol.*, 2(11):1441-1449 (2016).
Scher et al., "Baseline CTC subtype to predict outcomes on mCRPC patients (pts) receiving enzalutamide (E) compared to abiraterone (A)," *J. Clin. Oncol.*, 35(Suppl.15):5070 (2017).
Scher et al., "Characterization of circulating tumor cells (CTCS) of metastatic castration resistant prostte cancer (MCRPC) patients in first, second & third line systemic therapies," *Annals Oncol.*, 25(Suppl. 4):iv58-iv84, Abstract 238P (2014).
Shaffer et al., "Circulating tumor cell analysis in patients with progressive castration-resistant prostate cancer," *Clin. Cancer Res.*, 13(7):2023-2029 (2007).
Sidaway, "Non-traditional CTCs indicate prognosis," *Nature Rev.*, 13(7):592 (2016).
Starlinger et al., "Discrimination between circulating endothelial cells and blood cell populations with overlapping phenotype reveals distinct regulation and predictive potential in cancer therapy," *Neoplasia*,13(10):980-990 (2011).
State of the Science Report, Highlights from the 19th Annual PCF Scientific Retreat, Oct. 2012, 21 pages.
Stemcell Technologies, "Frequencies of Cell Types in Human Peripheral Blood," retrieved on Jun. 8, 2012, via Wayback Machine, 1 page.
Strijbos et al., "Circulating endothelial cells in oncology: pitfalls and promises," *Br. J. Cancer*, 98:1731-1735 (2008).
Tockman et al., "Considerations in bringing a cancer biomarker to clinical application," *Cancer Res.*, 52:2711s-2718s (1992).
Tufman et al., "Biological markers in lung cancer: A clinician's perspective," *Cancer Biomarkers*, 6(3-4):123-135 (2009).
Ulmer et al., "Immunomagnetic enrichment, genomic characterization, and prognostic impact of circulating melanoma cells," *Clin. Cancer Res.*, 15(2):531-537 (2004).
Vollebergh et al., "Genomic patterns resembling BRCA1- and BRCA2-mutated breast cancers predict benefit of intensified carboplatin-based chemotherapy," *Breast Cancer Res.*, 16(3):R47 (2014).
Wang et al., "Identification and characterization of circulating prostate carcinoma cells," *Cancer*, 88(12):2787-2795 (2000).
Watkins et al., "Genomica scars as biomarkers of homologous recombination deficiency and drug response in breast and ovarian cancers," *Breast Cancer Res.*, 16(3):211 (2014).
Wendel et al., "Fluid biopsy for circulating tumor cell identification in patients with early-and late-stage non-small cell lung cancer: a glimpse into lung cancer biology," *Phys. Biol.*, 9(1):016005 (2012).
Werner et al., "Analytical Validation and Capabilities of the Epic CTC Platform: Enrichment-Free Circulating Tumour Cell Detection and Characterization," *J. Circ. Biomark.*, 4:3 (2015).
Wong et al., "Evolution of androgen receptor targeted therapy for advanced prostate cancer," *Nat. Rev. Clin. Oncol.*, 11:365-376 (2014).
Woywodt et al., "Isolation and enumeration of circulating endothelial cells by immnomagnetic isolation: proposal of a definition and a consensus protocol," *J. Thromb. Heaemost.*, 4:671-677 (2006).
Zafarana et al., "Copy number alterations of c-MYC and PTEN are prognostic factors for relapse after prostate cancer radiotherapy," *Cancer*, 118(16):4053-4062 (2012).
Zhao et al., CN 101226118 b, machine translation to English, 2010, 22 pages.
Zhau et al., "Epithelial to mesenchymal transition (EMT) in human prostate cancer: lessons learned from ARCaP model," *Clin. Exp. Metastasis*, 25(6):601-610 (2008).
Zlotta et al., "Prevalence of prostate cancer on autopsy: cross-sectyional study on unscreened Caucasian and Asian men," *J. Natl. Cancer Inst.*, 105(14):1050-1058 (2013).
Deng et al., "Enrichment with anti-cytokeratin alone or combined with anti-EpCAM antibodies significantly increases the sensitivity for circulating tumor cell detection in metastatic breast cancer patients," Breast Cancer Res., 10(4):R69 (2008).
Fehm et al., "Cytogenetic evidence that circulating epithelial cells in patients with carcinoma are malignant," Clin. Cancer Res., 8:2073-2084 (2002).

\* cited by examiner

METHOD OF USING NON-RARE CELLS TO DETECT RARE CELLS

This application is a continuation of application Ser. No. 15/601,696, filed May 22, 2017, which is a continuation of application Ser. No. 13/503,014, which is the U.S. national stage of international application No. PCT/US2010/053431, filed Oct. 20, 2010, which claims the benefit of U.S. provisional application No. 61/253,787, filed Oct. 21, 2009, and is a continuation-in-part of application Ser. No. 15/710,102, filed Sep. 20, 2017, which is a continuation of application Ser. No. 12/223,351, which is the U.S. national stage of international application No. PCT/US2007/002798, filed Jan. 30, 2007, which claims the benefit of U.S. provisional application No. 60/763,625, filed Jan. 30, 2006, the entire contents of each of which are incorporated herein by reference.

BACKGROUND OF THE INVENTION

Field of the Invention

The invention relates generally to medical diagnostics and more specifically to detection and categorization of rare cells, such as circulating tumor cells (CTCs).

Background Information

Significant unmet medical need exists for the longitudinal disease monitoring in patients with epithelial cancers at the cellular level. Predicting and monitoring therapy response and disease progression are particularly important in epithelial cancer patients due to the natural history of the disease and the selective selection process in response to the therapeutic pressure. While progress has been made in understanding the primary and metastatic tumors in their respective microenvironments, a substantial barrier exists in understanding carcinoma behavior during the fluid phase, as it spreads within and occupies the bloodstream. The circulating component of cancer contains within it the cells giving rise to future metastases, and as such, represents a compelling target for investigation.

Research to fully characterize the clinical significance of this fluid phase of solid tumors has been hindered by the lack of easily accessible and reliable experimental tools for the identification of CTCs. The unknown character and low and unknown frequency of CTCs in the blood, combined with the difficulty of distinguishing between cancerous versus normal epithelial cells, has significantly impeded research into how the fluid phase might be clinically important. The ideal fluid phase biopsy should find significant numbers of a specific CTC population in most epithelial cancer patients and preserve and present CTCs to a pathologist and/or researcher in a format that enables not only enumeration but further molecular, morphologic and/or phenotypic analysis. In addition, it should preserve the remaining rare populations for further analysis.

CTCs are generally, although not exclusively, epithelial cells that originate from a solid tumor in very low concentration and enter into the blood stream of patients with various types of cancer. CTCs are also thought to be capable of originating in the blood, forming small colonies throughout the body. The shedding of CTCs by an existing tumor or metastasis often results in formation of secondary tumors. Secondary tumors typically go undetected and lead to 90% of all cancer deaths. Circulating tumor cells provide the link between the primary and metastatic tumors. This leads to the promise of using the identification and characterization of circulating tumor cells for the early detection and treatment management of metastatic epithelial malignancies. Detection of CTCs in cancer patients offers an effective tool in early diagnosis of primary or secondary cancer growth and determining the prognosis of cancer patients undergoing cancer treatment because number and characterization of CTCs present in the blood of such patients has been correlated with overall prognosis and response to therapy. Accordingly, CTCs serve as an early indicator of tumor expansion or metastasis before the appearance of clinical symptoms.

While the detection of CTCs has important prognostic and potential therapeutic implications in the management and treatment of cancer, because of their occult nature in the bloodstream, these rare cells are not easily detected. CTCs were first described in the 1800s, however only recent technological advances have allowed their reliable detection. The challenge in the detection of circulating tumor cells is that they are present in relatively low frequency compared to other nucleated cells, commonly less than 1:100,000. To compensate for this challenge, most conventional approaches for detecting circulating tumor cells rely on experimental enrichment methods, whereby the CTCs are preferentially separated from the other cellular components (e.g., non-CTCs), most importantly other nucleated cells that are the most similar to CTCs.

Currently, the most utilized methods of positive enrichment for enumeration/characterization of CTCs are immunomagnetic enrichment methods targeting the surface protein EpCAM and the "CTC chip". The most widely used methodology to detect CTCs, J&J's Veridex technology, utilizes immunomagnetic enrichment. The technology relies upon immunomagnetic enrichment of tumor cell populations using magnetic ferrofluids linked to an antibody which binds epithelial cell adhesion molecule (EpCAM), expressed only on epithelial derived cells. This methodology requires 7.5 mL of blood for analysis and finds greater than 2 CTCs in only some metastatic cancer patients.

Microfluidic or "CTC-Chip" technology, is another positive enrichment method for enumeration/characterization of CTCs. The methods utilizes 1-3 mL of blood in which whole blood flows past 78,000 EpCAM-coated microposts. EpCAM+ cells stick to the posts and are subsequently stained with cytokeratin, CD45, and DAPI. With this methodology, CTCs are found in virtually all metastatic cancer patients at a relatively high purity and not in healthy controls. Additionally, CTC-chip technology identifies CTCs in all patients and in higher numbers than other technologies by a factor of approximately 10 to 100 fold as reported in two recent publications.

The only routinely used technology for CTC detection is based on immunomagnetic enrichment. This current "gold standard" and FDA approved test is called CellSearch® and employs an immunomagnetic enrichment step to isolate cells that express the epithelial cells adhesion molecule (EpCAM). Additionally, to be identified as a CTC, the cell must contain a nucleus, express cytoplasmic cytokeratin, and have a diameter larger than five microns. This system has uncovered the prognostic utility of enumerating and monitoring CTC counts in patients with metastatic breast, prostate, and colorectal cancers; however, the sensitivity of this system is low, finding no or few CTCs in most patients. Most follow-on CTC technologies have reported higher sensitivity and are pursuing variations of the enrichment strategy, however this directly biases the detectable events towards those that have sufficient expression of the protein selected for the initial enrichment step.

A standardized microscope based approach has also been previously utilized to identify and morphologically characterize and credential CTCs in case studies of breast, colorectal, and lung cancer patients.

Although many CTC detection approaches are currently in use, significant limitations have been identified with the current approaches. For example, one significant limitation of positive selection methods to enumerate/characterize CTCs is that positive physical selection invariably leads to loss of CTCs and is less than 100% efficient. Thus the number of CTCs detected per sample using current methods is often too low to provide robust interpretation or clinically meaningful content of a particular sample. Additional limitations of current methods include low CTC detection due to CTC heterogeneity. For example, differences in individual CTC features within the CTC population of interest further hinder the number of CTCs detected using current methodologies. Such differences may include size variations between individual CTCs, and variable or down regulated expression between individual CTCs of the cell surface markers used to detect CTCs. A further limitation of existing methodologies includes limitations in purity levels and variable purity. Any enrichment will have a certain number of false positives, for instance other nucleated blood cells that stick to the enrichment. For example, the Veridex magnet has typically 5,000 to 10,000 false positives on top of the 5 to 10 positives.

SUMMARY OF THE INVENTION

The present invention is based in part on the discovery of innovative methods for analyzing samples to detect, enumerate and characterize rare cells, such as CTCs. Accordingly, the present invention provides methods for improved detection and characterization allowing for clinically meaningful analysis of samples for use in clinical, research and development settings.

Accordingly, the present invention provides methods for the improved detection and characterization of rare cells in a sample by utilizing data from non-rare cells (cells present at a concentration of 10, 50, 100, 200, 300, 400, 500, 1,000, 5,000, 10,000 times or greater as compared to the rare cell) in the sample. Thus the method of the invention utilizes similarity measures to assess non-similarity of cells, requiring both the biggest distance exclusion, e.g., events that are clearly non-rare cell related and the fine distinction of a cutoff based on similarities of surrounding non-rare cells.

The method includes providing a sample suspected of having at least one rare cell and at least one cell that is present at a concentration that is at least 10 times that of the rare cell; contacting the sample with at least one detectable agent, such as an agent that binds a cell marker; performing cell imaging on the sample to generate an image; and detecting the at least one rare cell as compared with other cells in the sample by analyzing the cell from the image, thereby detecting the rare cell in the sample. In various aspects of the invention, the method further includes plating of the suspected rare cell and at least one cell on a solid support, such as a slide, to facilitate contacting the cells with the detectable agent and cell imaging. In various aspects of the invention, the detectable agent is any agent used to stain the cells, such as an agent that binds a cell marker, including, but not limited to, a positive marker, negative marker, nuclear marker, content marker, or any combination thereof.

In various aspects of the invention, the methods described herein are performed on an apparatus for efficiently imaging a slide containing a detectable signal, such as a fluorescent signal. The apparatus may typically include a computer having at least one system processor with image processing capability, a computer monitor, an input device, a power supply and a microscope subsystem. Thus the apparatus includes a computer having executable code for performing the various analysis required to practice the invention. The microscope subsystem includes an optical sensing array for acquiring images. A two-dimensional motion stage for sample movement and for focus adjustment, and input and output mechanisms for multiple sample analysis and storage. The apparatus may also include a transmitted light source as well as an illuminating/fluorescent excitation light source for fluorescing samples.

In one embodiment of the invention, the method includes establishing optimal exposure limits for performing the cell imaging that facilitate detection of rare cells present. In one aspect, the exposure limit for the detectable agent is determined using a signal from at least one cell. In various aspects, the detectable marker may be a positive marker, negative marker, nuclear marker or content marker. In a related aspect, the exposure limits may be set using data relating to the cells and/or suspected rare cells gathered from a first image, to re-image the slide.

In another embodiment, the method includes minimizing exposure settings to minimize data collection time and maximize throughput to facilitate detection of rare cells.

In another embodiment, the method includes utilizing data associated with non-rare cells to generate a quality control parameter that facilitates detection of rare cells. In various aspects, the quality control parameter is distribution of at least one non-rare cell on the slide, alignment of multiple cell images via alignment of non-rare cell markers, quality of cell staining, distribution of a positive marker throughout the non-rare cells, or cell loss from repeated processing.

In another embodiment, the method includes determining intensity cut-off limits to minimize false negatives, as well as false positives and to facilitate rare cell detection. In one aspect, the detectable agent is a positive marker and the intensity limits are determined using mean, standard deviation, coefficient of variation, other statistical parameters or any combination thereof, for a background signal of the positive marker. In another aspect, the detectable agent is a positive marker and the intensity limits are determined within a single image, or portions of that image, by identifying the highest signal event from a positive marker and comparing the highest signal to the mean and standard deviation calculated from signals of all, or a subset of events. In yet another aspect, the detectable agent is a negative marker and the intensity limit for the negative marker is determined using mean and standard deviation of signals from the negative markers from non-rare cells (either all non-rare cells or a specific subset).

In another embodiment, cytological features of non-rare cells, such as cellular and nuclear size (absolute and relative; overall and apparent) and distribution, are utilized to facilitate detection of non-rare cells.

In another embodiment, the method includes utilizing data associated with non-rare cells to enumerate rare cells, thus facilitating their detection. In various embodiments, data may include, but is not limited to, total intensity, mean intensity, segmented intensity, fixed circle, variable circle, or any combination thereof.

In another embodiment, the method includes determination of the expression level of a content marker in rare cells and non-rare cells to facilitate detection of rare cells.

In various aspects of the invention, a rare cell is a CTC or subpopulation thereof.

As such, in another embodiment, the invention provides a method for diagnosing or prognosing cancer in a subject. The method includes performing the method of improved detection and characterization of CTCs as described herein and analyzing detected CTCs and provide a diagnosis or prognosis based on analysis of the CTCs, thereby diagnosing or prognosing cancer in a subject.

In another embodiment, the invention provides a method for determining responsiveness of a subject to a therapeutic regime. The method includes performing the method of improved detection and characterization of CTCs as described herein and analyzing the CTCs, thereby determining the responsiveness of the subject to a therapeutic regime.

In another embodiment, the invention provides a method for determining a candidate subject for a clinical trial. The method includes performing the method of improved detection and characterization of CTCs as described herein and analyzing the CTCs, thereby determining a candidate subject for a clinical trial.

DETAILED DESCRIPTION OF THE INVENTION

Figure 1:
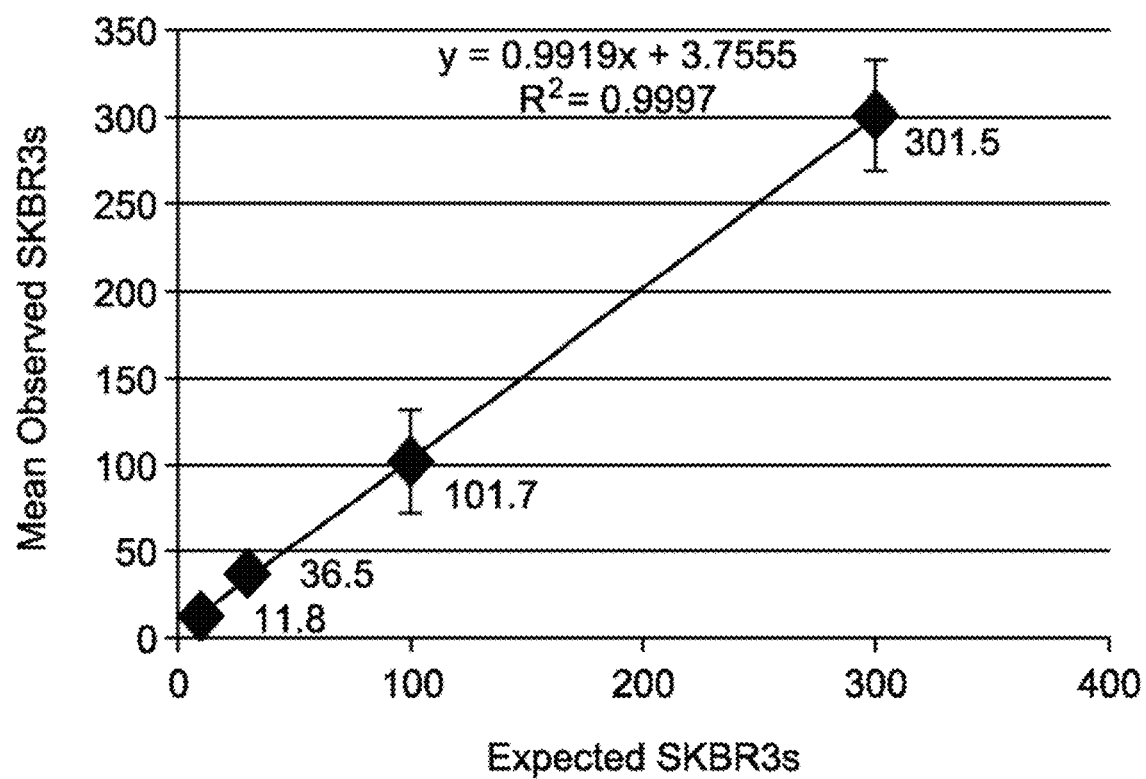
FIG. 1 is a graphical representation of mean observed SKBR3s plotted against expected SKBR3s. Four aliquots of normal control blood were spiked with varying numbers of SKBR2 cells to produce 4 slides with approximately 10, 30, 100, and 300 cancer cells per slide. The mean of each quadruplicate is displayed as well as error bars noting standard deviation.

The present invention provides a method which omits physical methods for positively emiching for rare cells, such as CTCs, from a mixed population, thereby minimizing the loss of rare cells. This methodology further allows for the capture/identification of subsets of cell populations, such as subpopulations of CTCs or other rare populations by detection of the same or different markers using different parameters, such as cutoff values, that allow for distinguishing between events and non-events. For example, as discussed in detail herein, different cutoffs may be utilized to characterize different cell subpopulations.

While the disclosure highlights CTCs and subpopulations thereof, the same methodologies may be used to find any other rare cell type in a background of non-rare cells. As used herein, a "rare cell" is intended to include a cell that is either 1) of a cell type that is less than about 5%, 4%, 3%, 2%, 1%, 0.1%, 0.01% or 0.001% of the total nucleated cell population in a fluid sample, or 2) of a cell type that is present at less than one million cells per milliliter of fluid sample. Exemplary rare cells include, but are not limited to CTCs, circulating endothelial cells (CECs), white blood cells in emboli, cancer stem cells, activated or infected cells, such as activated or infected blood cells, and fetal cells.

Accordingly, it will be understood by one in the art that references to CTCs throughout the specification include reference to rare cells and vice versa.

The present method allows for identification of rare cells, such as CTCs or subpopulations of CTCs from the background of other blood cells using microscopy, cytometry, automation, and computation. The present invention utilizes these components, individually and collectively, to identify rare cells. The benefits include the ability to find more rare cells, to present them in a way that enables subsequent analyses for content markers, and to do so in a time and resource efficient manner.

Further, the present disclosure is based in part on a next generation assay capable of identifying subpopulations of CTCs in cancer patients. One particular subpopulation identified was from a small cohort of cancer patients. In addition to using specific parameters defining subpopulations of CTCs, such as one referred to herein as the High-Definition-CTC (HD-CTC) subpopulation, the assay affords greater sensitivity with a smaller volume of blood than previous efforts. The key innovative aspects of this assay are driven by the need for simplicity and minimal processing of the blood specimen as well as conforming to the need to enable professional interpretation with diagnostic quality imagery.

The approach used to identify a rare cell population, such as CTCs, or subpopulation thereof, is distinct in that it does not rely on any single protein enrichment strategies. All nucleated blood cells are imaged in multiple colors to locate and morphologically evaluate rare events. This enrichment-free strategy results in an assay capable of 'tunable specificity/sensitivity' allowing high sensitivity and high specificity while still enabling the study of a rare cell population known to be heterogeneous. A key advantage and difference to physical enrichment is that one may 'tune' the outcome, while physical enrichment is 'yes' or 'no'. Another key advantage of this approach is that one or multiple analysis parameters can be pursued to identify and characterize specific populations of interest.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

In general, reference to "a circulating tumor cell" is intended to refer to a single cell, while reference to "circulating tumor cells" or "cluster of circulating tumor cells" is intended to refer to more than one cell. However, one of skill in the art would understand that reference to "circulating tumor cells" is intended to include a population of circulating tumor cells including one or more circulating tumor cells.

The term "circulating tumor cell" (CTC) or CTC "cluster" is intended to mean any cancer cell or cluster of cancer cells that is found in a subject's sample. Typically CTCs have been exfoliated from a solid tumor. As such, CTCs are often epithelial cells shed from solid tumors found in very low concentrations in the circulation of patients with advanced cancers. CTCs may also be mesothelial from sarcomas or melanocytes from melanomas. CTCs may also be cells originating from a primary, secondary, or tertiary tumor. CTCs may also be circulating cancer stem cells. While the term "circulating tumor cell" (CTC) or CTC "cluster" includes cancer cells, it also is intended to include non-tumor cells that are not commonly found in circulation, for example, circulating epithelial or endothelial cells. Accordingly tumor cells and non-tumor epithelial cells are encompassed within the definition of CTCs.

The term "cancer" as used herein, includes a variety of cancer types which are well known in the art, including but not limited to, dysplasias, hyperplasias, solid tumors and hematopoietic cancers. Many types of cancers are known to metastasize and shed circulating tumor cells or be metastatic, for example, a secondary cancer resulting from a primary cancer that has metastasized. Additional cancers may include, but are not limited to, the following organs or systems: brain, cardiac, lung, gastrointestinal, genitourinary tract, liver, bone, nervous system, gynecological, hematologic, skin, breast, and adrenal glands. Additional types of cancer cells include gliomas (Schwannoma, glioblastoma, astrocytoma), neuroblastoma, pheochromocytoma, paraganlioma, meningioma, adrenalcortical carcinoma, medulloblastoma, rhabdomyoscarcoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia; and skin cancers including malignant melanoma, basal cell carcinoma, squamous cell carcinoma, Karposi's sarcoma, moles dysplastic nevi, lipoma, angioma, dermatofibroma, keloids, sarcomas such as fibrosarcoma or hemangiosarcoma, and melanoma.

Using the methods described herein, rare cells, such as CTCs may be detected and characterized from any suitable sample type. As used herein, the term "sample" refers to any sample suitable for the methods provided by the present invention. The sample may be any sample that includes rare cells suitable for detection. Sources of samples include whole blood, bone marrow, pleural fluid, peritoneal fluid, central spinal fluid, urine, saliva and bronchial washes. In one aspect, the sample is a blood sample, including, for example, whole blood or any fraction or component thereof.

A blood sample, suitable for use with the present invention may be extracted from any source known that includes blood cells or components thereof, such as venous, arterial, peripheral, tissue, cord, and the like. For example, a sample may be obtained and processed using well known and routine clinical methods (e.g., procedures for drawing and processing whole blood). In one aspect, an exemplary sample may be peripheral blood drawn from a subject with cancer.

The term "blood component" is intended to include any component of whole blood, including red blood cells, white blood cells, platelets, endothelial cells, mestheial cells or epithelial cells. Blood components also include the components of plasma, such as proteins, lipids, nucleic acids, and carbohydrates, and any other cells that may be present in blood, due to pregnancy, organ transplant, infection, injury, or disease.

As used herein, a "white blood cell" is a leukocyte, or a cell of the hematopoietic lineage that is not a reticulocyte or platelet. Leukocytes can include nature killer cells ("AK cells") and lymphocytes, such as B lymphocytes ("B cells") or T lymphocytes ("T cells"). Leukocytes can also include phagocytic cells, such as monocytes, macrophages, and granulocytes, including basophils, eosinophils and neutrophils. Leukocytes can also comprise mast cells.

As used herein, a "red blood cell" or "RBC" is an erythrocyte. Unless designated a "nucleated red blood cell" ("nRBC") or "fetal nucleated red blood cell", as used herein, "red blood cell" is used to mean a non-nucleated red blood cell.

The present invention provides a method whereby a biological sample may be assayed or examined in many different ways to detect and characterize rare cells. A sample may be stained or labeled with one or more detectable markers and examined by fluorescent microscopy and/or light microscopy. Unlike conventional enrichment schemes whose goal it is to eliminate the non-rare or non-CTCs from evaluation, the present invention relies on the non-rare cells or non-CTCs present in the sample to aid in the identification and characterization of the rare cells or CTCs. In the presently described non-enrichment method, the sample (e.g., blood or other body fluid, including urine, peritoneal, pleural, saliva, cerebral spinal, and the like) is minimally processed, and the rare cells, such as CTCs are not separated from other nucleated cells (e.g., non-rare or non-CTCs).

As used herein, the terms "non-rare cell" and "non-rare cells", generally refer to any cell that is not a rare cell as defined herein. Similarly, as used herein, the terms "non-CTC" and "non-CTCs", generally refer to any cell that is not a CTC as defined herein. Non-rare and non-CTCs may include nucleated or enucleated cells, such as, in the case of blood, white blood cells (also called leukocytes) including neutrophils, eosinophils, basophils, lymphocytes, and monocytes; red blood cells (also known as erythrocytes); and platelets.

In the case of blood, while the CTCs may not be separated from other nucleated cells, red blood cells, which are typically only found nucleated in the blood of newborns, are removed from the sample before plating. This is commonly performed by lysing the red blood cells, although several alternative approaches are well known in the literature and may be utilized with the present methods, for example, removing the cells by filtration or density gradient centrifugation. After removing the red blood cells, the remaining cells may be processed by spinning, re-suspending, and plating the cells onto a solid support that may be used in cell imaging.

A variety of solid supports are well known in the art and include slides that may be treated to promote cellular attachment to the slide surface. The slide may be constructed from a variety of materials sufficient to provide a support for performing a biological assay. In an exemplary aspect, the support is composed of a material that may be coated with a compound that promotes electrostatic interaction of biological material to the support. A variety of substrate materials are well known in the art and suitable for use with the present invention. Such materials may include one or more of glass; organoplastics such as polycarbonate and polymethylmethacrylate, polyolefins; polyamides; polyesters; silicones; polyurethanes; epoxies; acrylics; polyacrylates; polyesters; polysulfones; polymethacrylates; polycarbonate; PEEK; polyimide; polystyrene; and fluoropolymers. In an exemplary aspect, the slide is manufactured from glass or plastic and includes one or more biologically interactive coatings.

Slides may include one or more active areas defined on the surface thereof. An active field, as used herein, is intended to include areas in which the slide has been chemically or electrically treated, such as with a biologically interactive coating, for example to promote the adhesion of cells to the slide. For example, the slide may be treated such that the surface is positively charged which allows for cells to be anchored to the surface though the electrostatic adhesion of a negatively charged cell. The slide may include from 1 to any number of active areas depending on the size of the slide and the intended application. In various aspects, the slide includes a single active area.

The total number of rare cells or CTCs that are adhered to a given slide is dependent, in part, on the initial sample volume. In various aspects, a wide range of initial sample volumes may be used to practice the present method and provide clinically significant results. As such, the initial sample volume may be less than about 1 μl, 2 μl, 2.5 μl, 3 μl, 4 μl, 5 μl, 6 μl, 7 μl, 7.5 μl, 8 μl, 9 μl, 10 μl, 12.5 μl, 15 μl, 17.5 μl, 20 μl, 25 μl, 50 μl, 75 μl, 100 μl, 125 μl, 150 μl, 175 μl, 200 μl, 225 μl, 250 μl, 300 μl, 400 μl, 500 μl, 750 μl, 1 ml, 2 ml, 3 ml, 4 ml, 5 ml, 6 ml, 7 ml, 8 ml, 9 ml or greater than about 10 ml. In an exemplary aspect, the initial sample volume is between about 200 and 500 μl, 200 and 1000 μl, 1000 to 2000 μl, 1000 to 3000 μl or 1000 to 5000 μl. In another exemplary aspect, a sample processed as described herein includes greater than about 1, 2, 5, 7, 10, 15, 20, 30, 40, 50, 100, 200, 300, 400, 500, 600, 700, 800, 900, or even 1000 rare cells or CTCs.

After adhering the minimally processed cells to a solid support, for example by plating the cells on a slide, the cells are contacted with one or more detectable markers to facilitate cell imaging via examination of the cells by fluorescent microscopy and/or light microscopy. In general, detectable markers include a variety of agents useful in detecting and characterizing cellular phenomenon. For example, detectable markers may include agents such as polynucleotides, polypeptides, small molecules, and/or antibodies that specifically bind to a marker present in a sample and which are labeled such that the agent is detectable when bound or hybridized to its target marker or ligand. For example, detectable markers may include enzymatic, fluorescent, or radionuclide labels. Additional reporter means and labels are well known in the art.

A marker can be any cell component present in a sample that is identifiable by known microscopic, histologic, or molecular biology techniques. Markers can be used, for example, to detect and characterize rare cells, including CTCs, and distinguish rare cells from non-rare cells and non-CTCs. In general a marker can be, for example, a molecule present on a cell surface, an overexpressed target protein, a nucleic acid mutation or a morphological characteristic of a cell present in a sample. Thus markers may include any cellular component that may be detected within or on the surface of a cell, or a macromolecule bound or aggregated to the surface of the cell. As such, markers are not limited to markers physically on the surface of a cell. For example, markers may include, but are not limited to surface antigens, transmembrane receptors or coreceptors, macromolecules bound to the surface, such as bound or aggregated proteins or carbohydrates, internal cellular components, such as cytoplasmic or nuclear components, and the like. A marker may also include a blood component that binds preferentially to specific cell types, such as platelets or fibrin.

In one aspect, a detectable marker may be a detectably labeled antibody. Antibodies useful in the methods of the invention include intact polyclonal or monoclonal antibodies, as well as any fragments thereof, such as Fab and F(ab')$_2$, as well as combinations of such antibodies or fragments. Methods for generating fluorescently labeled antibodies are well known in the art, for example, fluorescent molecules may be bound to an immunoglobulin either directly or indirectly by using an intermediate functional group. In related aspects, a detectable marker may be a nucleic acid molecule (e.g., an oligonucleotide or polynucleotide). For example, in situ nucleic acid hybridization techniques are well known in the art and can be used to identify an RNA or DNA marker present in a sample or subsample (e.g., individual cell).

In various aspects of the invention, the detectable markers used to stain the cells include one or more detectable markers that are tissue specific and thus used as a positive marker for a specific type of cell and/or tissue. As used herein, a "positive marker" is a detectable marker that specifically binds to a rare cell such as a CTC, but not a non-rare cell or non-CTC. For instance the positive marker may be epithelial and/or tissue specific, for example, cytokeratin and/or EpCAM marker may be used which bind preferentially to epithelial cells. Similarly, markers that are tissue specific may be employed. There are numerous examples of tissue-specific markers known in the art and suitable for use in practicing the invention, such as PSA and PSMA for prostate tissue, CDX2 for colon tissue and TTF1 for lung tissue (of the subpopulation of lung cancer patients that are TTF1 positive). As used herein a "positive marker" may also be a detectable marker that specifically binds to subpopulations of rare cells or CTCs, but not all rare cells or CTCs of a population. For example, a "positive marker" may specifically bind to HD-CTCs, but not all CTCs.

In various aspects of the invention, the detectable markers used to stain the cells include one or more detectable markers that specifically bind to non-rare cells or non-CTCs and may be used as a negative selector. As used herein a "negative marker" is a detectable marker that specifically binds to non-rare cells or non-CTCs and is a negative selector. The most commonly used negative marker for non-CTCs is CD45, which binds preferentially to WBCs. There are other detectable markers or combinations of detectable markers that bind to the various subpopulations of WBCs. These may be used in various combinations, including in combination with or as an alternative to CD45. As used herein a "negative marker" may also be a detectable marker that specifically binds to subpopulations of non-rare cells or non-CTCs and is a negative selector.

In addition to positive and negative detectable markers to identify CTCs, additional detectable markers may be used to stain cells that specifically bind to the nucleus of the cell allowing differentiation of cells from non-cellular material. As used herein, a "nuclear marker" is a detectable marker that binds to a nuclear component of a cell and allows differentiation of cells from non-cellular material. The most common nuclear marker for use in the present invention is DAPI.

In various aspects of the invention, the detectable markers used to stain the cells include one or more detectable markers referred to herein as "content markers". Content markers typically may include, detectably labeled oligonucleotide probes, such as FISH probes or immunohistochemistry probes. In one embodiment, content markers are applied to the slide at the same time as the positive and negative markers, or are applied to the slide after the positive and negative markers and after the identification of the rare cells by imaging. Content markers include detectable markers directed to EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or leukocyte associated receptor (LAR). In some cases, a content marker may also be a positive marker.

The intensity of signal from a positive marker, or any marker, is detectable on a scale of intensities, which based on the methodology of the disclosure, is highly quantifiable. The scale of intensity allows for vastly improved quantification and ranking of detectable events enabling further categorization. For example, a CTC that emits a low intensity signal for cytokeratin may be a cancer stem cell; or the change in the number of high/low cytokeratin cells might be either predictive of response or a readout of response (or resistance course). The same is true for positive, negative and content markers.

The present invention utilizes detectable markers to facilitate cell imaging via examination of the cells by fluorescent microscopy and/or light microscopy. In an exemplary aspect, the minimally processed cells are stained with several fluorescent markers, and then imaged using a fast, automated microscope. Typically, a prepared slide may be loaded onto the automated system or may be placed in a slide carrier that holds any number of additional slides. The slide carriers are loaded into an input hopper of the automated system. An operator may then enter data identifying the size, shape, and location of a scan area on each slide or the system can automatically locate a scan area for each slide during slide processing. The processing parameters of the slide may be identified by a bar code present on the slide or slide carrier. At system activation, a slide carrier is positioned on an X-Y stage, the entire slide, or portion thereof, is rapidly scanned. This may be done at low or high magnification and may be repeated at various levels of magnification and/or for various regions of the slide. Images may be stored on an appropriate storage medium and analyzed using executable code as is well known in the art for performing the various analysis discussed herein. As discussed herein, various parameters may be adjusted throughout the imaging process to facilitate detection of rare cells, for example, CTCs using data regarding non-rare or non-CTCs, such as exposure limits and intensity settings.

As used herein, the terms "image" and "sample image" generally refer to an image, digital or otherwise, of a minimally processed sample including various cells, such as rare cells and CTCs. Typically, a sample image is an image of all or a portion of a sample slide having cells adhered to its surface and optionally stained with one or more detectable markers.

One advantage of the present invention, which allows for tunable specificity/sensitivity and focuses on data reduction and analysis rather than enrichment, is that minimal processing is expected to minimize bias. In alternative techniques that require enrichment, rare cells are invariably lost in the process. Specifically, in the use of immunocapture or size filtration to distinguish between WBCs and CTCs, variation in the expression of the targeted antigen in the case of immunocapture or variation in the size differential between the WBC and CTC causes some CTCs to be lost during the enrichment phase. This can lead to (i) inaccurate counts of CTCs; (ii) too few CTCs for downstream characterization or content analysis; and (iii) the creation of a selection bias as some types of CTCs are preferentially lost based upon their type of variation.

The challenge with the minimal processing approach is that it is difficult to find the low frequency rare cells or CTCs in the background of the non-rare cells or non-CTCs. The low frequency may be 1 rare cell or CTC:1,000 non-rare cells or non-CTCs, 1:10,000, 1:100,000, 1:1,000,000, and even 1:10,000,000, or anywhere between those ratios. Complicating the ability to find and characterize the rare cells is that the positive and negative markers, while very selective, are not perfect resulting in either false positives or false negatives. In other words, it is common to have some background staining of the negative markers on the rare cells and/or some background staining of the positive markers on the non-rare cells. While assay optimization is used to minimize this background staining, it is challenging to completely eliminate the phenomenon with assay optimization.

As mentioned previously, most other approaches for finding rare cells attempt to remove the non-rare cells. The present invention uses the non-rare cells or non-CTCs to aid in finding and characterizing the rare cells or CTCs. The numerous ways in which non-rare cells and non-CTCs may be analyzed are discussed throughout the disclosure. Throughout this disclosure, non-rare cells or non-CTCs are typically referred to as a single group and may be analyzed using the methods described herein as such. However, the invention also recognizes that non-rare cells may contain various discrete subgroups. For example, in the case of CTCs, the various discrete subgroups may include neutrophils, macrophages, lymphocytes, eosinophils and basophils, and cells in varying states such as various states of apoptosis or cell division, that may be distinguished using the methods described herein by size, shape, nuclear characteristics, and staining pattern. In some embodiments of the invention, it may be useful to use one of these subgroups to aid in finding rare cells or CTCs, rather than to use the entire group. The use of non-rare or non-CTCs in the present invention is not meant to limit the invention to using only the entire group when it may be appropriate in some of the embodiments to use just one or more of the subgroups.

An enabling aspect of this invention is that the low frequency of rare cells or CTCs to non rare cells or non-CTCs allows one to treat the majority of cells as non-rare cells or non-CTCs even if they have not been definitively identified as such. The low frequency of rare cells and CTCs allows one to ignore such cells and assume the cells are non-rare cells or non-CTCs to derive quality control, cut-off, normalization, and calibration metrics. Since the rare cells are in low abundance, if these metrics are to be refined taking into consideration the population of rare cells, outlier removal techniques may be utilized. The outlier removal techniques mathematically ensure that the population of rare cells does not factor into the metrics.

As discussed herein, the disclosed methodology allows detection, enumeration and characterization of populations of rare cells or subpopulations of rare cells. The methodology utilizes data from non-rare cells in the sample to identify and characterize rare cells by applying defined parameters pertaining to exposure limits, exposure settings, quality control, intensity cut-off limits, cell size and shape calibration, cell enumeration and content evaluation, each of which is further discussed in turn. In various aspects, the assay allows for simultaneous cytomorphologic review of fluorescent images with individual channel images, augmented with cell-by-cell annotation with ancillary semi-quantitative data regarding size and fluorescent intensity of objects both absolute and relative to the non-rare cells or non-rare cell candidates, e.g., non-CTCs or non-CTC candidates, from either the full experiment or the local environment.

Establishing Exposure Limits.

While variation should be minimized through assay optimization and instrument standardization, variation in the staining of the markers is common, slide-to-slide, batch-to-batch, operator-to-operator, and day-to-day. Thus selecting the right exposure for a particular slide is non-trivial, as setting it too low or too high will cause one to miss information. While standard approaches work for those markers that are common on the majority of events on the slide, it is challenging for those that are specific to rare cells or CTCs. Within the dynamic range of the imaging system, the signal in rare cells or CTCs and background in non-rare cells or non-CTCs are proportional to the exposure time. But noise which is random variation in both signal and background caused by electronics in the imaging system decreases when exposure increases. Ideally, exposure should be set to maximize the signal without saturating the imaging system. But this is impractical due to the impact on data collection time. Because a rare cell or CTC is present in very low frequency, it is unlikely that a rare cell or CTC would be found in a small number of Sample Images, preventing one from using the Sample Images to set the exposure for the positive marker. Complicating this further, there is a natural variation in the expression of and staining of both positive and negative markers to their target cells. A small number of Sample Images to set exposure may not capture this natural variation on the target rare cells or CTCs.

In one embodiment of this invention, the signal from the non-rare cells or non-CTCs is utilized to set the exposure limit for the positive marker. This is somewhat counter-intuitive as the non-rare cell or non-CTC is not the target of choice for the positive marker. However in this embodiment, the exposure is adjusted so that a visible but low signal is observed from the non-rare cells or non-CTCs in the Sample Images originating from fluorescent sources such as non-specific staining, autofluorescence and optical system properties. The brightfield imagery, nuclear marker and the negative marker may be used to identify the non-rare cells or non-CTCs in the Sample Images. The low signal is a distinguishable cellular signal in the non-rare cells or non-CTCs when compared to the non-cellular areas in the Sample Image. This process provides a method to set the exposure for the positive marker when the target of those markers are in low frequency and also helps to maximize the Signal/Background of the positive marker, both of which are aids to finding rare cells or CTCs while still minimizing the total time required to collect data. This phenomenon is especially true when the signal is low or dim. Once cellular background is statistically significant above non-cellular background, the exposure time for this particular marker is optimized for speed of data collection. All subsequent optimization can be performed in silico. Once the exposure is set, the entire slide is ready to be imaged at that setting.

While the above embodiment facilitates the setting of exposure for the positive marker, non-rare cells or non-CTCs may also be used to set the exposure for the negative markers, nuclear markers and content markers in a way that is relevant for the clinical interpretation of rare cells or CTCs. In one embodiment, the nuclear marker on non-rare cells or non-CTCs in the Sample Images is set to a level that allows the evaluation of the nuclear content of a cell, and in particular whether the cell is classified as live or dead, facilitating the calculations of live:dead ratios for cells by cell type. These exposure levels for the nuclear marker for the non-rare cells or non-CTCs will be satisfactory for the same evaluation of the nuclear marker for the rare cells or CTCs, in particular to distinguish nuclear shape on normal vs. malignant cells.

In another embodiment, the exposure for the negative marker is set from the Sample Images by looking at the distribution of the signal from that marker on the non-rare or non-CTCs where the exposure is chosen to maximize the signal/background ratio, especially at the critical low end of the dynamic range where a faint signal to a negative marker in a rare cell or CTC may occur.

In another embodiment, the exposure is set from the non-rare cells or non-CTCs for the content marker. The setting of the signal for the content marker using the non-rare cells or non-CTCs in Sample Images will depend on the specific content marker. For instance, some content markers may have relatively high expression in the non-rare cells or non-CTCs when compared to rare cells or CTCs, in which case one would use the information from the non-rare cells or non-CTCs in the Sample Images to set the upper boundary for the content marker. Conversely, the content marker may have relatively low expression in the non-rare cells or non-CTCs when compared to the rare cells or CTCs, in which case one would use the information from the non-rare cells or non-CTCs in the Sample Images to set the lower boundary for the content marker.

While the above embodiments use non-rare cells or non-CTCs to set the exposure limits from Sample Images for various markers prior to imaging the slide to find rare cells or CTCs, in another embodiment information from the non-rare cells or non-CTCs and/or rare cells or CTCs from the images taken during the first imaging event of the entire slide is used to set the exposure limits when selected areas of the slide are re-imaged. Selected areas are re-imaged for a variety of reasons, including collecting images that are in optimal focus or that are in a higher magnification. In this embodiment, the distribution of signals for the various markers in the non-rare cells or non-CTCs and the rare cells or CTCs across the entire slide may be used to calculate a better exposure that maximizes the desired signal or the desired dynamic range.

Minimizing Exposure Setting to Minimize Data Collection Time and Maximize Throughput.

As described above, exposure settings can be adjusted to optimize the signal or signal:background parameters. However, in another embodiment, exposure settings are adjusted with a goal of minimizing data collection time and maximizing throughput. For example, one might determine that it takes 5 seconds of exposure time to fully utilize the dynamic range of the CCD camera but only 500 milliseconds to get the cellular background above the non-cellular background, hence saving 10× data collection time. Thus exposure times can be optimized either for maximum signal (or signal:background) or for minimum time.

Quality Control.

In another embodiment, the use of non-rare cells or non-CTCs to aid in identifying rare cells or CTCs also includes their use as quality control parameters. Since the non-rare cells or non-CTCs are represented in much higher frequency and distributed throughout the slide, they provide an available resource to evaluate the quality of the processing and imaging of the slide, both relative to a particular slide as well as across slides and across data sets.

In one embodiment, the invention provides observing the distribution of the non-rare cells or non-CTCs using the nuclear markers to identify the non-rare cells or non-CTCs. In this embodiment, the goal is to find cells, not necessarily to distinguish between non-rare cells or non-CTCs and rare cells or CTCs, and thus the positive or negative markers may not be utilized to distinguish between these categories; however, since the vast majority of the cells are non-rare cells or non-CTCs, most of the cells that utilized to determine distribution of cells on the slide are non-rare cells or non-CTCs. The distribution of the cells is important from a quality control standpoint as the desired distribution is an even distribution of cells with minimal overlap between the cells. If there is a substantial deviation from that ideal distribution, one may elect to reject the slide from further processing. While a nuclear marker is used in this example, any method for identifying the cells would suffice, including brightfield imaging and conventional stains such as Wright Giemsa.

In another embodiment, the co-location of the nuclear marker and the negative marker is used as a quality control method to evaluate whether the alignment of different images is satisfactory. In this embodiment, the nuclear marker and the negative marker should have significant overlap.

In another embodiment, the ratio between negative marker events and the nuclear marker events is a measure for the effectiveness of the negative marker staining, where the higher the ratio without exceeding 12 is desirable. A desirable negative marker may have a 0.8, 0.9, 1.0 or 1.1 ratio. In another embodiment, the distribution, including mean, standard deviation and coefficient of variation (CV) of the negative marker over the population of the non-rare cells or non-CTCs is used as a quality control parameter, where the distribution of the negative marker is consistent with expected distribution patterns of past experiments and/or consistent with the distribution of WBC's normal expression patterns.

In another embodiment, the distribution, including mean, standard deviation and CV of the positive marker over the population of the non-rare cells or non-CTCs is used as a quality control parameter, where the distribution of the positive marker is consistent with expected distribution patterns from past experiments.

While the quality control methods described above describe methods to evaluate overall slide quality, the same methods may be used to evaluate an image or a group of images. In some instances, the parameters derived from an image or a group of images in a region may be compared to the same parameters calculated over the entire slide. In another instance, the quality control parameters described above may be compared across different slides.

In another embodiment, cell loss may be calculated from the slide during processing by comparing the ratio of the nuclear marker events or negative marker events to the known number of non-rare cells or non-CTCs placed on the slide, where the known number of non-rare cells or non-CTCs is derived from the WBC count and the volume used in the experiment.

Setting Intensity Cut-Off Limits for CTC Detection (Minimizing False Negatives).

As mentioned above, the challenges in this approach to rare cell and CTC detection are 1) that the relative frequency of rare cells, such as CTCs, to non-rare cells or non-CTCs is low; and 2) the imperfect staining of the positive and negative markers to CTCs and non-CTCs respectively. However, the present method takes those challenges and turns them into strengths. In one embodiment, the background signal from the positive markers on the highly abundant non-rare cells or non-CTCs is used to calculate mean, standard deviation and CV. Those metrics are subsequently used to determine detection cut-offs to separate rare cells, such as CTCs from non-rare cells or non-CTCs. In one aspect, the factor of 10 multiplied by the standard deviation and added to the mean for the non-rare cell or non-CTC positive marker signal, is used as a cut-off to distinguish rare cells or CTCs, where putative rare cells or CTCs are determined to have a positive marker signal greater than that cut-off. In other aspects, the metric uses a factor of 5, 7.5, 12.5, 15, 17.5, 20 or more, or any number between those numbers. The calculation of the metric may be set on a global slide basis. Alternatively, it may be set on an image basis or a regional basis.

In another embodiment, the cut-off may be determined dynamically within each image by locating a signal of the highest positive marker events, then comparing that signal to the standard deviation between additional signal events. In an exemplary aspect, the cut-off may be determined dynamically within each image by locating signals of the five highest positive marker events, then comparing that signal to the standard deviation between the next fifty positive signal events. Positive marker events can also include multiple positive markers or inclusion of positive markers and exclusion of negative marker events. The number 'five' could be varied from 1 to 10 per field of view assuming a 10× magnification (i.e., assuming no more than 5 rare cells or CTCs per field of view or a relative concentration of no more than 1 in 500). This approach has the advantage of being entirely numerical and not being based on shape analysis. It is expected to robustly and substantially reduce the number of possible events with minimal risk of missing events.

In another embodiment, the cut-off for the negative marker signal is set using the mean and standard deviation of the non-rare cells or non-CTCs. In this case, the cut-off is derived from a factor of 1, 2, 3, 4, 5, 6, 7, 8, 9 or 10 multiplied by the standard deviation of the negative marker signal for the non-rare cells or non-CTCs and subtracted from the mean negative marker signal. Putative CTCs will have a negative marker signal below that cut-off. As described above, this cut-off may be generated globally by using the signal from all non-rare cells or non-CTCs on the slide or at the image or regional level by using the signal only from the non-rare cells or non-CTCs in that image or that region.

Size and Shape Calibration.

In another embodiment of the invention, the cellular size and distribution of cell sizes for the non-rare cells or non-CTCs as measured on the slide is compared to the published sizes and distributions for the WBCs in the literature. In addition, the distribution may be corrected for individual patient differences by using differential count of the subgroups of the WBCs obtained from an automated cell counter. The ratio between the published size and the calculated size of the non-rare cells or non-CTCs may then be used as a correction factor to determine an accurate size for the rare cells or CTCs by multiplying that ratio with by the size of the rare cell or CTC as measured on the slide. Calibration allows for standardization and comparisons across slides and across blood tubes and across patients and across indications.

In another embodiment, we compare one or more of the nuclear size, distribution of nuclear size, and contour patterns for non-rare cells or non-CTCs as measured on an image or slide to nuclear size and contour pattern of a putative rare cell or CTC and apply cut-off values to qualify that putative rare cell or CTC as a valid rare cell or CTC.

Enumeration.

In an embodiment of the invention, the non-rare cells or non-CTC information is used to accurately calculate the concentration of rare cells or CTCs in a bodily fluid. In one example of this embodiment, one determines the ratio of CTCs to total CTCs+non-CTCs (all nuclear marker events) and then divides that by the volume of the original body fluid used for that experiment, and filially multiply that by the original concentration of the cells in the body fluid. The later measurement may be obtained through the use of a standard automated cell counter (or cytometer).

Content Evaluation.

As mentioned above, the rare cell or CTC expression level of a content marker may be evaluated. However, because of the slide variability caused by processing and imaging variation, it is difficult to provide universal parameters to determine the expression level. To mitigate this challenge, the expression level of the content marker and its distribution in non-rare cells or non-CTCs in a patient population is first determined. Then for the individual cancer patient, the expression level of the content marker in rare cells or CTCs and in non-rare cells or non-CTCs is determined. The ratio of the expression level between rare cells or CTCs and non-rare cells or non-CTCs becomes a relative measure that normalizes slide-to-slide variation. In addition, multiplying that ratio by the mean non-rare cell or non-CTC expression level from the control population provides for an absolute value for the rare cell or CTC expression corrected for slide-to-slide variation.

Nuclear shape and size is a potential rich source of information. It is expected to give detailed information about the type of cell in the case of a blood cell and about the state of the cell in the case of a are cell or CTC. For example, nuclear shape could give insight to the malignant nature of the cell, it could give insight into the state of cell viability and/or cell cycle. For example, a patient undergoing a successful chemotherapy might see a spike in CTCs but nuclear interpretation might show that these CTCs are non-viable/apoptotic.

Another potential opportunity for using nuclear size and shape would be similar to FACS analyses using forward scatter and side scatter as ways to characterize cells. It may be possible to gather enough detailed information about the nucleus and other cellular components to recapitulate the forward and side scatter information from FACS.

In various embodiments of the invention, a single or combination of parameters may be utilized in performing the assay depending, in part on the data to be determined and the rare cell population being investigated. Additionally, subpopulations of specific rare cell populations may be identified using the disclosed methodology. For example, as shown in Example 1, subpopulations of CTCs may be identified and differentiated by further defining specific assay parameters. The Example discloses identification and classification of a CDC subpopulation referred to as HD-CTC.

In one embodiment of the invention, by further defining parameters of the disclosed assay, a strict classification the HD-CTC was established. Without being bound to any particular theory, it is believed that the HD-CTC subpopulation as classified herein, includes CTCs exhibiting the highest potential of becoming an intact tumor cell. All other CTCs partially fulfill the defined parameters but lack one or more of the strict inclusion criteria. Non-HD-CTCs are CTCs which may be less reliable in evaluation performed in further downstream methodologies.

In one embodiment, an HD-CTC is a cell that comprises a) a positive marker; b) has an intact nucleus; and c) is morphologically distinct from normal WBCs, wherein the cell is not positive for a negative marker. As discussed herein, the positive marker may be a marker that preferentially binds to epithelial cells, such as cytokeratin and/or EpCAM. Further, as discussed herein, the negative marker may be any non-cancer specific marker, such as CD45 which preferentially binds to WBCs. Determination of an intact nucleus is typically determined by DAPI imaging, but other suitable nuclear markers are well known in the art. In an exemplary embodiment, an HD-CTC is a cell that is a) cytokeratin positive; b) CD45 negative; c) has an intact nucleus; and d) is morphologically distinct from normal WBCs.

In various embodiments, the positive marker may have an intensity that is greater than 1, 2, 3, 4, 5, 6, 7, 8, 9 or 10 times that of a nucleated white blood cells' cytokeratin intensity. In various embodiments, the intensity of the negative marker is in the lowest 10%, 5%, 4%, 3%, 2% or less of all cellular events.

In various embodiments, the nucleus of a HD-CTC is intact and non-apoptotic. Mild apoptotic changes in the cytoplasm are accepted, as long as the nucleus does not appear apoptotic.

Figure 2:
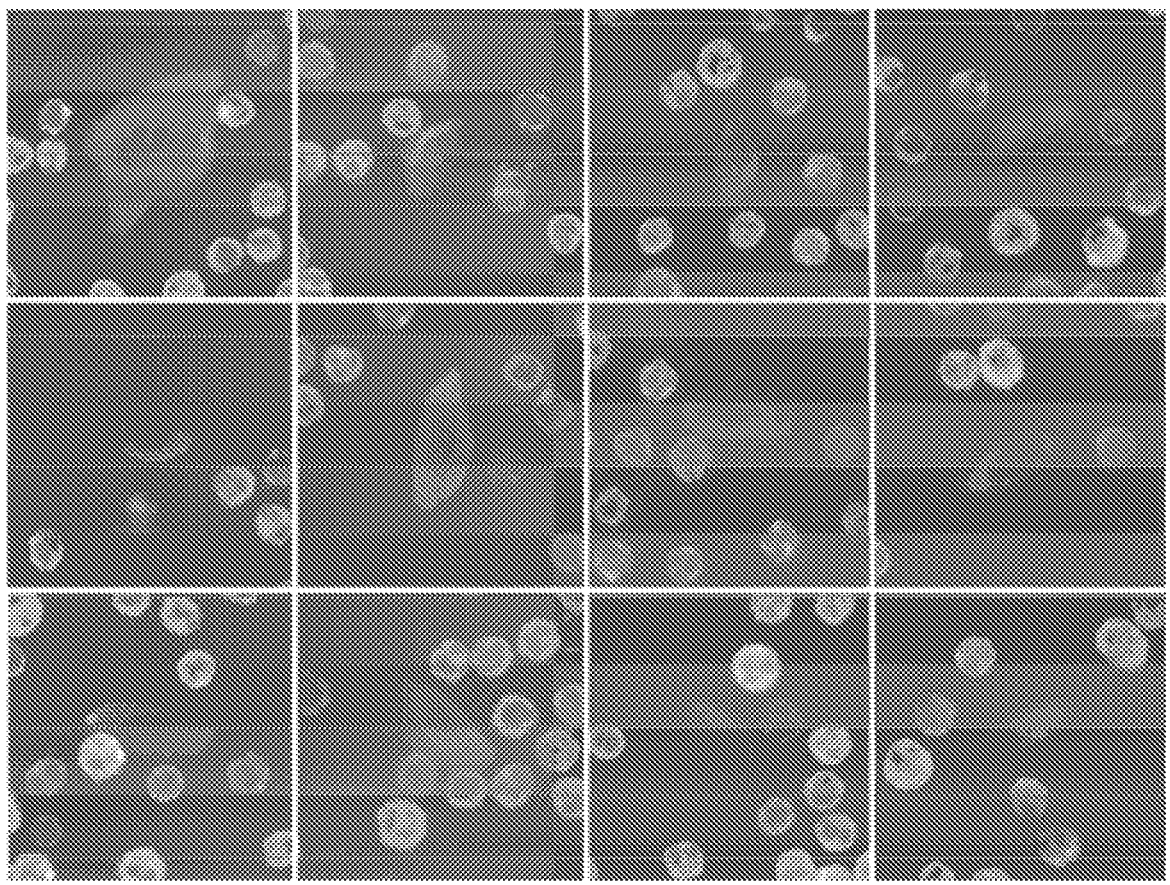
FIG. 2 is a pictorial representation of a gallery of a representative subpopulation of CTCs found in cancer patients. Each CTC of the subpopulation is cytokeratin positive, CD45 negative, contains a DAPI nucleus, and is morphologically distinct from surrounding white blood cells which are circular in shape.

In various embodiments HD-CTCs are morphologically distinct from normal WBCs. For example, HD-CTCs may have a morphology that is consistent with a malignant epithelial cell by criteria used in standard diagnostic cytopathology, predominantly embodied as enlarged size, but that may also include cytomorphologic features, such as, architectural organization of nucleus and cytoplasm, cytoplasmic shape, and nuclear shape. A gallery of representative HD-CTCs is displayed in FIG. 2.

While the methods described in this invention are useful in detecting rare cells using data derived from analysis of non-rare cells, as discussed throughout, the invention also is useful in characterization of rare cells. In particular, use of the various combinations of detectable markers and computational methods for performing cell imaging and analysis allow for meaningful characterization useful in assessing cancer prognosis and in monitoring therapeutic efficacy for early detection of treatment failure that may lead to disease relapse. In addition, CTC analysis according to the invention enables the detection of early relapse in presymptomatic patients who have completed a course of therapy. This is possible because the presence of CTCs has been associated and/or correlated with tumor progression and spread, poor response to therapy, relapse of disease, and/or decreased survival over a period of time. Thus, enumeration and characterization of revealed CTCs provides methods to stratify patients for baseline characteristics that predict initial risk and subsequent risk based upon response to therapy.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Accordingly, in another embodiment, the invention provides a method for diagnosing or prognosing cancer in a subject. The method includes detecting CTCs as described herein. CTCs may then be analyzed to diagnose or prognose cancer in the subject. As such, the methods of the present invention may be used, for example, to evaluate cancer patients and those at risk for cancer. In any of the methods of diagnosis or prognosis described herein, either the presence or the absence of one or more indicators of cancer, such as, a cancer cell, or of any other disorder, may be used to generate a diagnosis or prognosis.

In one aspect, a blood sample is drawn from the patient and processed to detect CTCs as described herein. Using the method of the invention, the number of CTCs in the blood sample is determined and the CTCs are characterized by analysis of the detectable markers and other data gathered from imaging the cells. For example, analysis may be performed to determine the number and characterization of CTCs in the sample, and from this measurement, the number of CTCs present in the initial blood sample may be determined.

In various aspects, analysis of a subject's CTC number and characterization may be made over a particular time course in various intervals to assess a subject's progression and pathology. For example, analysis may be performed at regular intervals such as one day, two days, three days, one week, two weeks, one month, two months, three months, six months, or one year, in order to track level and characterization of circulating epithelial cells as a function of time. In the case of existing cancer patients, this provides a useful indication of the progression of the disease and assists medical practitioners in making appropriate therapeutic choices based on the increase, decrease, or lack of change in circulating epithelial cells, such as the presence of CTCs in the patient's bloodstream. Any increase, be it 2-fold, 5-fold, 10-fold or higher, in the number of CTCs over time decreases the patient's prognosis and is an early indicator that the patient should change therapy. Similarly, any increase, be it 2-fold, 5-fold, 10-fold or higher, indicates that a patient should undergo further testing such as imaging to further assess prognosis and response to therapy. Any decrease, be it 2-fold, 5-fold, 10-fold or higher, in the number of CTCs over time shows disease stabilization and a patient's response to therapy, and is an indicator to not change therapy. For those at risk of cancer, a sudden increase in the number of CTCs detected may provide an early warning that the patient has developed a tumor thus providing an early diagnosis. In one embodiment, the detection of revealed CTCs increases the staging of the cancer.

In any of the methods provided herein, additional analysis may also be performed to characterize CTCs, to provide additional clinical assessment. For example, in addition to image analysis, gene expression analysis and PCR techniques may be employed, such as gene chip analysis and multiplexing with primers specific for particular cancer markers to obtain information such as the type of tumor, from which the CTCs originated, metastatic state, and degree of malignancy. Additionally, cell size, DNA or RNA analysis, proteome analysis, or metabolome analysis may be performed as a means of assessing additional information regarding characterization of the patient's cancer. In various aspects, analysis includes antibodies directed to or PCR multiplexing using primers specific for one or more of the following markers: EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR).

For example, the additional analysis may provide data sufficient to make determinations of responsiveness of a subject to a particular therapeutic regime, or for determining the effectiveness of a candidate agent in the treatment of cancer. Accordingly, the present invention provides a method of determining responsiveness of a subject to a particular therapeutic regime or determining the effectiveness of a candidate agent in the treatment of cancer by detecting CTCs of the subject as described herein and analyzing the detected CTCs. For example, once a drug treatment is administered to a patient, it is possible to determine the efficacy of the drug treatment using the methods of the invention. For example, a sample taken from the patient before the drug treatment, as well as one or more cellular samples taken from the patient concurrently with or subsequent to the drug treatment, may be processed using the methods of the invention. By comparing the results of the analysis of each processed sample, one may determine the efficacy of the drug treatment or the responsiveness of the patient to the agent. In this manner, early identification may be made of failed compounds or early validation may be made of promising compounds.

Four important indicators that provide insight to the clinical activity of candidate compounds include HER2, EGFR, CXCR4, and EphB4 RTK. HER2 provides an indicator of malignancy of a cell by determining mRNA stability and subcellular localization of HER2 transcripts. The resistance of EGFR to acquire mutations, and/or the mutations acquired provides important indicators of the activity of a candidate compound in addition to possible alternative compounds that may be used in combination with the candidate compound. An assessment of the level of DNA repair interference induced with platinum provides insight as to the status of the CXCR4 marker and metastatic condition. Additionally, assessment of the status of EphB4 receptor tyrosine kinase provides insight as to the metastatic potential of the cell. Accordingly, using the methods of the present invention, patients taking such candidate drugs may be monitored by taking frequent samples of blood and determining the number of circulating epithelial cells, for example CTCs, in each sample as a function of time. A further analysis of the Her2, EGFR, CXCR4, and EphB4 RTK indicators provides information as to pathology of the cancer and efficacy of the candidate drug. Similarly, ERRC1, Cytokeratin, PSA, PSMA, RRM1, Androgen Receptor, Estrogen Receptor, Progesterone Receptor, IGF1, cMET, EML4 and others provide insight into the clinical activity of candidate compounds. The analysis of these indicators of clinical activity may be through analysis of detectable markers as discussed herein (e.g., immunohistochemistry and fluorescent in situ hybridization (FISH)) or further analysis via techniques such as sequencing, genotyping, gene expression or other molecular analytical technique.

Analysis of CTCs provide a method of determining candidate subjects for a particular clinical trial. For example, the detected CTCs of a candidate may be analyzed to determine whether specific markers exist in order to determine whether the particular therapeutic regime of the clinical trail may be potentially successful. Accordingly in another embodiment, the invention provides a method for determining a candidate subject for a clinical trial. The method includes detecting CTCs of the subject as described herein. The CTCs may then be analyzed to determine whether the candidate subject is suitable for the particular clinical trial.

Analysis of CTCs during a clinical trial will provide information on whether the patient is responding or not responding to the experimental drug, where no substantial change or a decrease in revealed CTCs indicates response and an increase in revealed CTCs indicates poor response. The increase or decrease may be 2-fold, 10-fold or higher. This information is an early indicator of the drug's effectiveness and may be used by the investigators as a secondary endpoint in the clinical trial.

The following examples are intended to illustrate but not limit the invention.

Example 1

CTC Assay and Identification of CTC Subpopulation

The data presented here demonstrate the methodology of the present invention as applied to CTCs and subpopulations of CTCs, such as HD-CTCs as defined herein. The assay is performed via a controlled prospective protocol to address the reliability and robustness of the assay as well as a split sample comparison with the Cellsearch®. After this technical validation, the assay was used to investigate the incidence and prevalence of CTCs and specific CTC subpopulations in patients with metastatic breast, prostate, and pancreatic cancers as well as normal controls. The specific subpopulation of CTCs targeted by the assay requires that the cell(s) have an intact nucleus, express cytokeratin and not CD45, are morphologically distinct from surrounding white blood cells (WBCs) and have cytologic features consistent with intact malignant epithelial cells suitable for downstream analysis.

The following methods and protocols were utilized.

Patients and Blood Sample Collection was performed as follows. Samples were collected from metastatic cancer patients in anti-coagulated blood tubes at Scripps Clinic. University of California, San Diego, Billings Clinic, and University of California, San Francisco under IRB approved protocols. Samples from non-local sites (UCSF, Billings Clinic) were shipped overnight so that the sample was received and processed within 24 hours. Samples from local sites (Scripps Clinic and UCSD) were held at room temperature for 16-24 hours to mimic samples coming from non-local sites. Blood specimens were also drawn from normal controls from the TSRI Normal Blood Donor Service.

Blood sample processing for HD-CTC detection was performed as follows. Blood specimens were rocked for 5 minutes before a white blood cell (WBC) count was measured using the Hemocue™ white blood cell system (HemoCue, Sweden). Based upon the WBC count, a volume of blood was subjected to erythrocyte lysis (ammonium chloride solution). After centrifugation, nucleated cells were re-suspended in PBS and attached as a monolayer on custom made glass slides (Marienfeld, Germany). The glass slides are the same size as standard microscopy slides but have a proprietary coating that allows maximal retention of live cells. Each slide can hold approximately 3 million nucleated cells, thus the number of cells plated per slide depended on the patients WBC count. Enough blood was lysed to produce 15 slides and the cells were subsequently dried onto the slides after a cell preservative was added. All 15 slides were stored at −80° C. for at least 24 hours.

For HD-CTC detection in cancer patients for this investigation, 4 slides were used as a test. The remaining slides created for each patient were stored at −80° C. for future experiments. Four slides were thawed from each patient, then cells were fixed with 2% paraformaldehyde, permeabilized with cold methanol, and non-specific binding sites were blocked with goat serum. Slides were subsequently incubated with monoclonal anti-pan cytokeratin antibody (Sigma) and CD45-Alexa 647 (Serotec). After PBS washes, slides were incubated with Alexa Fluor 555 goat anti-mouse antibody (Invitrogen). Cells were counterstained with DAPI and mounted with an aqueous mounting media.

Imaging and technical analysis was performed as follows. All four slides from each patient were scanned using a custom made fluorescent scanning microscope which has been developed and optimized for fast, reliable scanning. One scanning instrument was used for all patient samples in this report to standardize results. Additionally, the light source was calibrated weekly and an algorithm was developed to standardize the exposures of each fluorophore on each patient slide during the scan. Each slide was scanned entirely at 10× magnification in 3 colors and produced over 6900 images. The resulting images were fed to an analysis algorithm that identifies likely candidate HD-CTCs based upon numerous measures, including cytokeratin intensity, CD45 intensity, as well as nuclear and cytoplasmic shape and size. A technical analyst then goes through algorithm generated likely candidates and removes hits that are obviously not cells, such as dye aggregates.

Professional analysis and interpretation was performed as follows. All likely candidate CTCs are presented to a hematopathologist for analysis and interpretation through a web based report where the pathologist is able to include or exclude each candidate cell as an HD-CTC. Cells are classified as HD-CTCs if they are cytokeratin positive, CD45 negative, contained an intact DAPI nucleus without identifiable apoptotic changes (blebbing, degenerated appearance) or a disrupted appearance, and are morphologically distinct from surrounding white blood cells (usually a shape based feature, although occasionally purely size based. They must have cytoplasm that is clearly circumferential and within which the entire nucleus is contained. The cytoplasm may show apoptotic changes such as blebbing and irregular density or mild disruption at the peripheral cytoplasmic boundary, but must not be so disrupted that its association with the nucleus is in question. The images are presented as a digital image, with individual fluorescent channel viewing capability as well as a composite image. Each cell image is annotated with ancillary statistical data regarding relative nuclear size, fluorescent intensities, and comparative fluorescent intensities. Each HD-CTC candidate is presented in a field of view with sufficient surrounding WBCS to allow for contextual comparison between cytomorphologic features of the cell in question versus the background white blood cells.

Cell line experiments were performed as follows. Four aliquots from the donor (2 ml each) were spiked with varying numbers of SKBR-3 cells to produce 4 slides with approximately 300, 100, 30 and 10 cancer cells per a slide. The 16 slides were then processed and analyzed by a single operator according to the HD-CTC sample preparation protocol. A single instrument was used to image all 16 slides.

HD-CTC Classification:

HD-CTCs were defined as cells that are a) cytokeratin positive (intensity >6 times that of nucleated white blood cells' cytokeratin intensity); b) CD45 negative (intensity in lowest 2% of all cellular events); c) include an intact non-apoptotic appearing nucleus by DAPI imaging; and d) are morphologically distinct from normal WBCs.

Inclusion requirements for the morphological assessment of HD-CTC include 1) a nuclear size 30% greater than the average surrounding WBC nuclei, and 2) circumferential cytokeratin positive cytoplasm with an average intensity 600% greater than surrounding nucleated WBCs. Common, although not required, features of HD-CTCs include quite large nuclei up to five times the average size of surrounding WBC nuclei, nuclear contours distinct from surrounding WBC nuclei including elongation, large cytoplasmic domain with a frequently eccentric distribution and/or polygonal or elongated cytoplasmic shape, and doublets and clusters of 3 or more HD-CTCs. Other cell-like objects that are cytokeratin positive, CD45 negative, and contain a nucleus but do not meet the inclusion criteria, for example are the same size as WBCs or have cytoplasm that is not circumferential, are not counted as HD-CTCs but are tracked by the assay. The purpose of this approach is to have strict inclusion criteria for a specific phenotype of CTCs, while retaining data about events that fulfill only some of the requirements, but which might still be clinically meaningful, such as apoptotic tumor cells or tumor cell fragments or cells undergoing epithelial to mesenchymal transition.

Results.

Assay Linearity and Sensitivity Using Spike-in Experiments:

To test assay linearity and sensitivity, specific dilutions ranging from 10 to 300 breast cancer cell line SKBR3s were spiked into normal control blood. Experiments were performed in quadruplicates and processed and analyzed according to the HD-CTC assay as explained in the Methods Section. The mean observed SKBR3s is plotted against expected SKBR3s and displays a correlation coefficient ($R^2$) of 0.9997 (FIG. 1).

Figure 3:
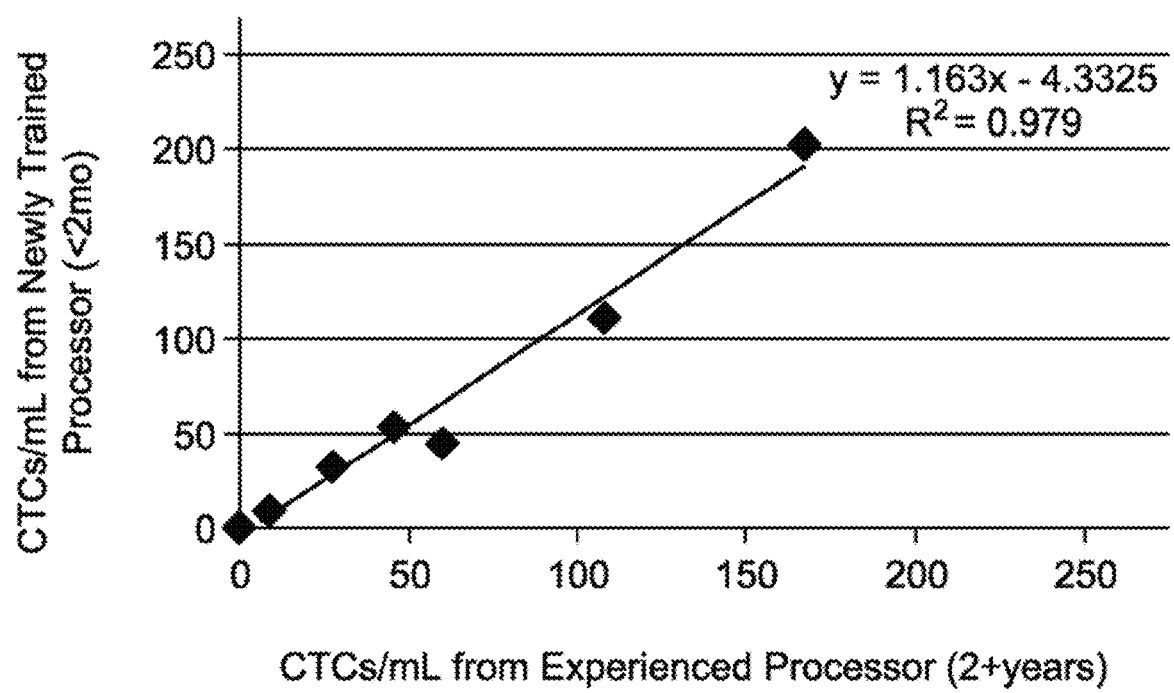
FIG. 3 is a graphical representation comparing CTC counts between two separate processors on 9 different cancer patient samples. CTC/mL counts ranged from 0 to 203.
Figure 4A:
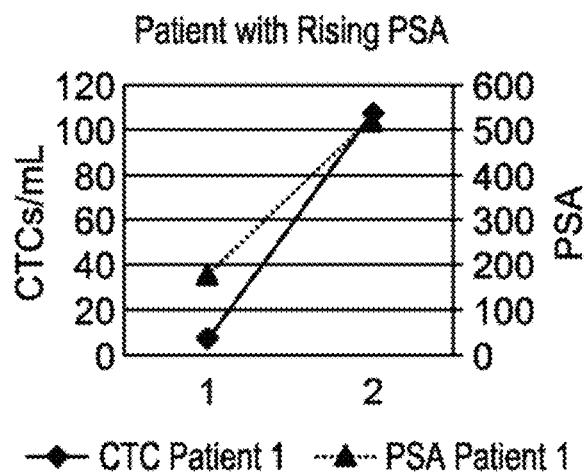
FIGS. 4A-4D are graphical representations including four graphs plotting CTC and PSA levels of serial blood draws from 4 different prostate cancer patients over a three month time period. Two patients had increasing CTC and PSA levels and two patients had decreasing/stable CTC and PSA levels. PSA levels increased in patients that had increasing CTC counts and decreased in patients that had decreasing/stable CTC counts.
Figure 4B:
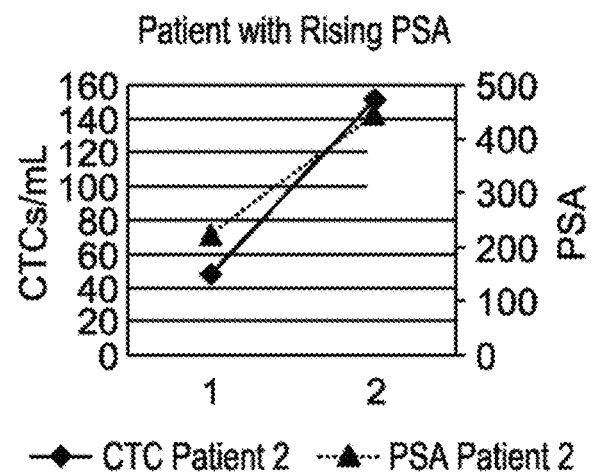
Figure 4C:
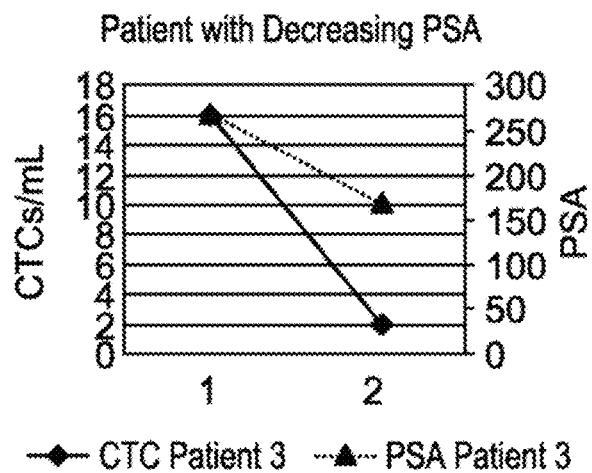
Figure 4D:
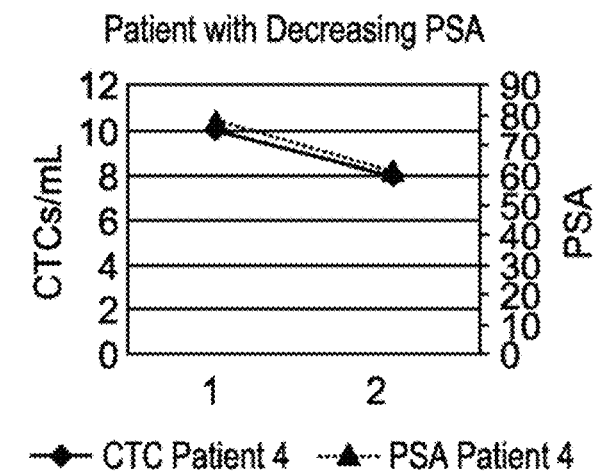

Assay Robustness of HD-CTC Counts in Patients with Carcinomas:

Assay robustness of the HD-CTC assay was tested against multiple processors and split samples. Duplicate tests were performed by two separate processors on 9 different patient samples. A comparison of HD-CTC/mL counts between two processors using split samples has a correlation coefficient ($R^2$) of 0.979 (FIG. 3). All data were analyzed by a single operator blinded to the experiment.

Assay Specificity in Samples from Normal Controls:

Fifteen healthy donors from an institutional healthy donor pool were evaluated as a control population consisting of 8 females and 7 males with an age range of 24 to 62 years. In all but one healthy control, the number of such events when corrected for volume was 1 HD-CTC/ml or less. The outlier was a healthy female donor with an HD-CTC count of 4/ml. Upon explicit review of her cells, about one third of them strongly met all inclusion criteria, while the remaining two thirds fulfilled all criteria but were near the lower limit for inclusion by one or more criteria. Four other healthy donors had 1 HD-CTC/ml. Explicit review of these cells revealed a similar pattern, in that about one third strongly met all criteria, while the remaining two thirds of the cells fulfilled criteria, but were near the lower limit for inclusion by one or more criteria. Examples of included events that are near the lower limit for inclusion are cells that measure 30% larger than surrounding WBCs but don't appear significantly larger by morphologic evaluation, and cells that are slightly out of focus and might have apoptotic nuclear changes that are not detectable by eye, and finally, occasional cells that have objective cytokeratin intensity measurements above the cutoff but subjectively don't appear significantly brighter than surrounding WBCs by single channel fluorescent review.

TABLE 1

Comparison of HD-CTC Assay to CellSearch ®

| Cancer Type | HD-CTCs/mL | CellSearch/mL |
|---|---|---|
| Breast #1 | 49.3 | 0.1 |
| Breast #2 | 87.0 | 0.0 |
| Breast #3 | 33.4 | 0.1 |
| Breast #4 | 199.3 | 0.1 |
| Breast #5 | 5.0 | 3.1 |
| Prostate #1 | 2.3 | 0.0 |
| Prostate #2 | 8.4 | 0.4 |
| Prostate #3 | 107.3 | 2.8 |
| Prostate #4 | 1.3 | 0.0 |
| Prostate #5 | 150.5 | 0.1 |
| Prostate #6 | 0.0 | 0.0 |
| Prostate #7 | 1.4 | 0.5 |
| Prostate #8 | 1.5 | 0.1 |
| Prostate #9 | 145.3 | 0.8 |
| Prostate #10 | 57.6 | 0.0 |

(Extrapolated to CTCs/mL)

Comparison of HD-CTC Assay to CellSearch®:

A total of 15 patients, 5 metastatic breast cancer and 10 metastatic prostate cancer, were evaluated for CTCs with both Cellsearch® and the HD-CTC assays. Two tubes of blood were collected from each patient. One tube of 7.5 mL of blood was collected in CellSave™ tubes (Veridex, Raritan N.J.) and sent to Quest Diagnostics (San Juan Capistrano, Calif.) for enumeration of CTCs using the Cellsearch® assay. A second tube of blood was collected from each patient and processed according to the HD-CTC protocol 24 hours after the blood draw, consistent with the standard HD-CTC process in order to mimic the timing at which samples were processed at Quest Diagnostics. The CellSearch® assay detected 2 or more CTCs per 7.5 mL of blood in 5/15 patients tested. In contrast, the HD-CTC assay detected significantly higher numbers of CTCs in significantly more patients (HD-CTCs were identified in 14/15 patients tested, Table 1).

Incidence of HD-CTCs in Patients with Metastatic Cancer:

HD-CTCs were also enumerated in an additional cohort of 30 metastatic breast cancer patients, 20 metastatic prostate cancer patients, 18 metastatic pancreatic cancer patients, and 15 normal controls. Using this approach, ≥5 HD-CTCs/mL were found in 80% of the prostate cancer patients (mean=92.2), 70% of the breast cancer patients (mean=56.8), 50% of the pancreatic cancer patients (mean=15.8), and 0% of normal controls (mean=0.6) (Table 2).

TABLE 2

Percentage of patients with HD-CTCs/mL of blood obtained from cohort.

| | N | ≥2 | ≥5 | ≥10 | ≥50 |
|---|---|---|---|---|---|
| Prostate | 20 | 90% | 80% | 65% | 40% |
| Breast | 30 | 80% | 70% | 60% | 27% |

TABLE 2-continued

Percentage of patients with HD-CTCs/mL of blood obtained from cohort.

|  | N | ≥2 | ≥5 | ≥10 | ≥50 |
|---|---|---|---|---|---|
| Pancreatic | 18 | 61% | 44% | 44% | 11% |
| Normal | 15 | 7% | 0% | 0% | 0% |

Morphology of HD-CTCs:

A heterogeneous population of CTCs within and across patients was observed. CTCs had various shapes, sizes, and cytokeratin intensities. In some cases, distinctive cytologic features such as large size or polygonal cytoplasmic shape, were quite distinctive and monotonous within the patient's sample. In other cases, there was cytomorphologic variability between HD-CTCs within a single sample. Cell size also varied; many patient samples had HD-CTCs with nuclei uniformly three or four times the size of neighboring WBC nuclei, while other patients had cells with nuclei only 1.3 times the size of neighboring WBC nuclei. Some patients had a range of sizes. A lower limit for HD-CTC nuclear size of 1.3 times the average WBC nucleus was selected based on evaluation of the largest nuclear size of cells we identified as WBCs showing false nonspecific staining with cytokeratin, for instance, CD45 positive and cytokeratin positive.

Interestingly, using this platform that allows for detailed morphologic evaluation, HD-CTC clusters were identified in the majority of the cancer patients (88%) in this cohort, ranging from clusters of 2 HD-CTCs to greater than 30 HD-CTCs (data not shown). Each HD-CTC was cytokeratin positive, CD45 negative, contained a DAPI nucleus, and was morphologically distinct from surrounding nucleated cells.

In addition to counting HD-CTCs, a number of different categories of cells were tracked including cells that had nuclei displaying apoptosis, cells that didn't have circumferential cytokeratin, other cells that were the same size or smaller than surrounding WBC, and cells that were cytokeratin dim or negative (images not shown). Specifically, some CTCs were excluded because they lacked various morphologic or morphometric inclusion criteria: including one or more of: a) cytokeratin intensity too dim; b) nuclear size too small; c) cytokeratin insufficiently circumferential (surrounds less than ⅔ of nucleus); d) cytokeratin too dim, although appears to be a cluster of two very large cells; e) nucleus shows apoptotic disintegration changes; f) nucleus too small and cytoplasm insufficiently circumferential; appears to be a cell in late apoptosis; g) nucleus too small (same size as surrounding WBC nuclei); h) cytokeratin present, but not circumferential; and i) cytoplasm insufficiently circumferential, nucleus too small.

Although many of these events may in fact represent circulating malignant epithelial cells in various stages of anoikis or disruption secondary to even the minimal processing utilized in the platform, the goal is to identify a 'pure' population of cells with a very high likelihood of representing intact circulating functional malignant potentially metastasizing epithelial cells that are suitable for downstream analysis by secondary methodologies. Fragmented, disrupted, pyknotic or otherwise damaged carcinoma cells are not considered evaluable in standard diagnostic pathology, and thus they are excluded in this fluid phase biopsy platform as well. They are enumerated and tracked, as it is recognized that their presence likely correlates overall with the tumor biology in the patient, either by reflecting overall tumor burden or by reflecting some as yet ill-understood complex equation involving tumor burden and tumor vascularity and efficiency of intravascular immune surveillance; however, they are not useful for secondary analysis, and thus they are not designated as HD-CTCs.

Many patients, in addition to having HD-CTCs, had a substantial number of cells that had nuclei that were morphologically distinct from surrounding WBC, resembled the nuclei of the HD-CTCs within that sample, and were CD45 negative, but were also cytokeratin dim or negative (data not shown). Representative types of CTCs found in a single prostate cancer patient included CTCs that were negative for cytokeratin and CD45, but exhibited a large nucleus similar to other CTCs found in this patient, typical CTCs that were cytokeratin positive, CD45 negative, and which had a DAPI nucleus, and CTC clusters of 4 cells.

In light of the extensive current debate about the possible existence of carcinoma cells undergoing epithelial-to-mesenchymal transition, the appearance and protein expression pattern of these cells identifies them as possible candidates for such a cell type.

Discussion.

The robustness of the HD-CTC platform was evaluated with both cell lines and patient samples. Despite little automation, and complete manual wetlab processing, of the current HD-CTC assay used for this cohort, the reproducibility of the assay is impressive with an average CV of less than 9% for 9 different samples processed by two independent technicians.

The criteria used to define a CTC are different across different technologies. The currently disclosed identified a subpopulation that has the highest likelihood of being bonafide tumor cells. Even with strict criteria, the incidence of CTCs using our assay is much higher than many technologies and in the same range as reported by the CTC-chip. Additionally, a head on comparison to CellSearch® showed significantly more CTCs in a higher proportion of patients. Whereas other technologies have observed occasional doublets and clusters of CTCs, clusters of CTCs were observed in most patients.

It is noteworthy that in the small cohort tested, the frequency of detection, and relative concentration, of CTCs among different tumor types using the methodologies of the invention (prostate>breast>pancreatic) parallels the findings observed using other methods such as CellSearch®.

Observationally, CTCs track over the clinical course of a small subset of prostate cancer patients in which serial draws were performed (FIG. 4). Serial HD-CTC detection may be embedded into therapeutic clinical trials. This is expected to allow study of patients with uniform clinical characteristics who are treated similarly and in whom long-term clinical follow-up will be performed. In addition to correlating these cells with patient outcomes to determine their prognostic and monitoring value, these HD-CTCs are expected to serve as a pharmacodynamic tool for assessing on-target effects at a molecular level of drugs of interest.

In summary, the instant example provides data that the HD-CTC assay (i) finds significant number of CTCs in most patients with metastatic cancer, (ii) has improved sensitivity over the Cellsearch® System, (iii) provides HD-CTCs in an ideal format for downstream characterization, (iii), enables the prospective collection of samples that can be stored frozen for long periods of time, and then retrospectively analyzed as new assays or markers become available.

Example 2

CTC Assay and Identification of Rare Cell Populations

The data presented here demonstrate identification of putative rare cell populations. Using the methodology described herein, a putative rare cell population was identified. Sample processing and imaging was performed as disclosed in Example 1. Additionally, HD-CTCs were identified and defined as in Example 1.

Figure 5:
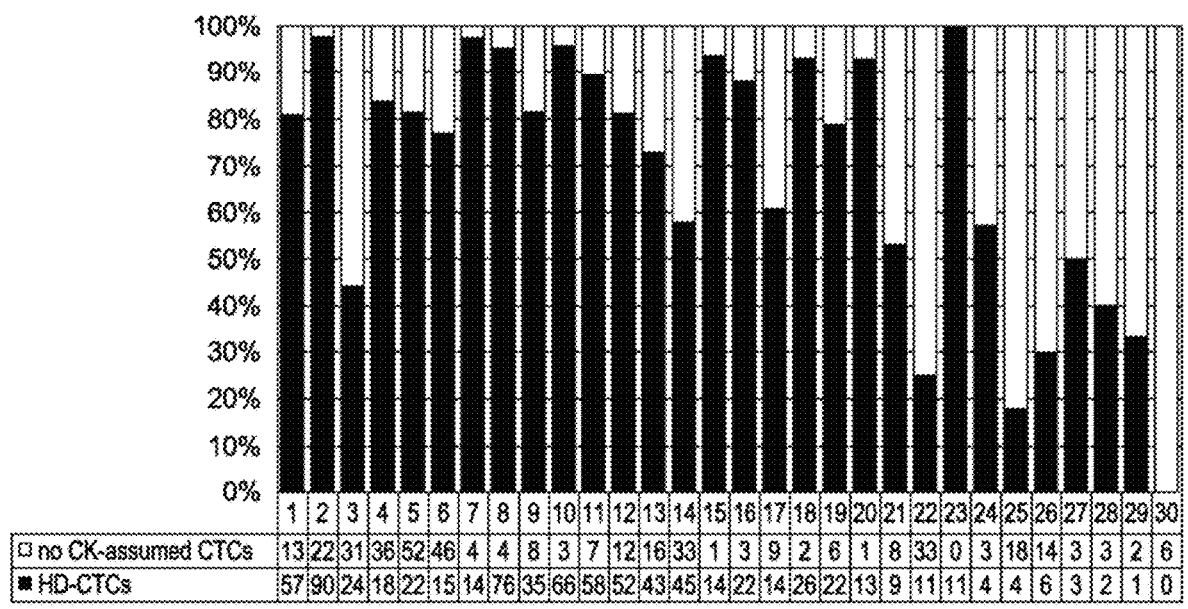
FIG. 5 is a graphical representation showing the incidence rate of a putative rare cell population across patients relative to a CTC subpopulation (HD-CTC).

In performing the assay, no CTCs were assumed to be cytokeratin positive. A putative rare cell population was identified having the following characteristics: a) cytokeratin dim or negative; b) CD45 negative; and c) intact non-apoptotic appearing nucleus by DAPI imaging. FIG. 5 displays the incidence rate of the putative rare cell population across patients relative to identified HD-CTCs.

Although the invention has been described, it will be understood that modifications and variations are encompassed within the spirit and scope of the invention. Accordingly, the invention is limited only by the following claims.

What is claimed is:

1. A method for detecting a circulating tumor cell (CTC) in a blood sample from a subject having metastatic cancer comprising:
   a) plating a non-enriched blood sample comprising nucleated blood cells onto a slide, said non-enriched sample suspected of comprising circulating tumor cell (CTCs) and non-CTCs wherein said non-CTCs are present at a concentration that is at least 10 times that of the CTCs;
   b) contacting the sample with a first immunuofluorescently detectable agent targeting a positive marker and a second immunuofluorescently detectable agent targeting a negative marker, wherein said positive marker is cytokeratin, wherein said negative marker is CD45, and wherein said detectable agent comprises an antibody;
   c) scanning the slide with fluorescent scanning microscopy to generate a cell image of the nucleated cells in the sample; and
   d) identifying the CTC in the sample based on assessment of said detectable agents and morphology in said cell image, wherein the CTC is cytokeratin positive, CD45 negative, has an intact nucleus, and is morphologically distinct from white blood cells.

2. The method of claim 1, wherein said positive marker is expressed on a specific cancer cell type or cancer tissue.

3. The method of claim 2, wherein said positive marker is expressed on a specific cancer cell type.

4. The method of claim 3, wherein said specific cell type is epithelial.

5. The method of claim 1, wherein said negative marker is expressed on non-CTCs.

6. The method of claim 5, wherein said non-CTCs are white blood cells.

7. The method of claim 1, further comprising a third immunofluorescently detectable agent.

8. The method of claim 7, wherein said third immunofluorescently detectable agent targets a content marker.

9. The method of claim 8, wherein said content marker is androgen receptor (AR).

* * * * *